United States Patent [19]

Dangman et al.

[11] Patent Number: 5,335,373
[45] Date of Patent: Aug. 9, 1994

[54] PROTECTIVE MEDICAL GLOVES AND METHODS FOR THEIR USE

[76] Inventors: Kenneth H. Dangman, 400 Riverside Dr. Apt. #1A, New York City, N.Y. 10032; Edward A. Jazlowiecki, P.O. Box 9333, 11 Lincoln Ave. Suite 6, Forestville, Conn. 06010

[21] Appl. No.: 800,487

[22] Filed: Nov. 29, 1991

[51] Int. Cl.$^5$ ............................................ A41D 19/00
[52] U.S. Cl. ...................................... 2/161.7; 2/167; 2/168; 604/292
[58] Field of Search ................... 2/167, 168, 169, 164, 2/161 R, 159, 161.7, 901; 128/292, 306, 307; 604/292

[56] References Cited

U.S. PATENT DOCUMENTS

| | | | |
|---|---|---|---|
| 2,541,103 | 2/1951 | Sander | 167/58 |
| 3,633,216 | 1/1972 | Schonholtz | 2/168 |
| 4,526,828 | 7/1985 | Fogt et al. | 2/167 X |
| 4,771,482 | 9/1988 | Shlenker | 2/168 X |
| 4,901,372 | 2/1990 | Pierce | 2/168 X |
| 4,919,966 | 4/1990 | Shlenker | 2/168 X |
| 4,935,260 | 6/1990 | Shlenker | 2/168 X |
| 5,003,628 | 4/1991 | Miyake et al. | 02/167 |
| 5,019,604 | 5/1991 | Lemole | 523/105 |
| 5,024,852 | 6/1991 | Busnel et al. | 2/168 X |
| 5,031,245 | 7/1991 | Milner | 2/168 |
| 5,045,341 | 9/1991 | Shlenker | 2/167 X |
| 5,128,168 | 7/1992 | Shlenker et al. | 2/167 X |
| 5,130,159 | 7/1992 | Shlenker et al. | 2/167 X |

FOREIGN PATENT DOCUMENTS

WO 91/10409 7/1991 PCT Int'l Appl. ................. 2/161 R
9014048 11/1990 World Int. Prop. O. ................. 2/21

OTHER PUBLICATIONS

Stecher, et al., "Nonoxynol", 1968 8th ed., The Merck Index, pp. 745.
Maki, "Lister Revisited: Surgical Antisepsis and Asepsis", 1976, New England Journal of Medicine, 294(3): pp. 1286–1287.
Viljanto, "Disinfection of Surgical Wounds Without Inhibition of Normal Wound Healing", 1980, Arch. Surg., 115, pp. 253–256.
Rodeheaver, et al., "Bactericidal Activity and Toxicity of Iodine-Containing Solutions in Wounds", 1982, Arch. Surg., 117, pp. 181–186.
Simmons, et al., "CDC Guidelines for the Prevention and Control of Nosocomial Infections" (Guideline for hospital environmental control), Am. Journal of Infection Control, 1983, 11[3], pp. 91–120.

(List continued on next page.)

Primary Examiner—Clifford D. Crowder
Assistant Examiner—Sara M. Current

[57] ABSTRACT

A protective medical glove containing a liquid antiseptic composition and methods for its use are disclosed. The flexible glove comprises at least a thin inner layer and at least a thin outer layer of material; the outer layer is preferably the more elastic and less plastic layer. Between the layers of the glove, a liquid antiseptic composition is stored which comprises an antiseptic in a liquid. The liquid antiseptic composition may also contain a surface-active agent, an algesic agent, a colorant, a vasoconstrictive agent, a smell-causing chemical, and a viscosity-modifying agent. A glove puncture by an object may cause some transfer of liquid antiseptic composition from the glove onto the hand and into a hand wound should the wound occur; useful as an immediate treatment to help to prevent a possible systemic infection by a pathogen in the individual; the treatment can help to protect a gloved individual such as a surgeon, a medical doctor, a health care worker or another worker whose work may place them at risk of becoming contaminated by a glove-puncturing object contaminated with the AIDS virus, hepatitus B virus or another infectious pathogen.

20 Claims, 8 Drawing Sheets

OTHER PUBLICATIONS

Simmons, et al., "CDC Guidelines for the Prevention and Control of Nosocomial Infections" (Guideline for prevention of surgical wound infections), Am. Journal of Infection Control, 1983, 11[4], pp. 133–143.

Hicks, et al., "Inactivation of HTLV–III/Lav–Infected Cultures or Normal Human Lymphocytes By Nonoxynol–9 in Vitro", 1985, Dec. 21/28, The Lancet, pp. 1422–1423.

Harvey, "Antiseptics and Disinfectants; Fungicides; Ectoparasiticides", 1985, In: The Pharmacological Basis of Therapeutics; 7th ed., Chapter 41, pp. 959–979.

Weiss, et al., "HTVL–III Infection Among Health Care Workers", 1985; The Journal of the Am. Med. Assoc., vol. 254, No. 15; pp. 2089–2093.

Rietmeijer et al., "Condoms as Physical and Chemical Barriers Against Human Immunodeficiency Virus," 1988, The Journal of the Am. Med. Assoc., 259[12], pp. 1851–1853.

Newsom, et al., "What is in the Surgeon's Glove?", 1988, Journal of Hospital Infection, 11[supplement A], pp. 244–259.

Bartlett, "Testing for HIV Infection: Recommendations for Surgeons", 1988, Am. College of Surgeons Bulletin, 73[3], pp. 4–10.

Gerberding, et al., "Risk of Exposure of Surgical Personnel to Patients' Blood During Surgery at San Francisco General Hospital", The New England Journal of Medicine. 1990. 322[25] pp. 1788–1793.

Monteflori, et al., "Effective Inactivation of Human Immunodeficiency Virus With Chlorhexidine Antiseptics Containing Detergents and Alcohol", 1990, Journal of Hospital Infection, 15, pp. 279–282.

Speller, et al., "Acquired Immune Deficiency Syndrome: Recommendations of a Working Party of the Hospital Infection Society", 1990, Journal of Hospital Infection, 15, pp. 7–34.

Sanders, et al., "Outer Gloves in Orthopaedic Procedures", 1990, The Journal of Bone and Joint Surgery, Inc., 72–A[6], pp. 914–917.

Closs & Tierney, "Theatre Gowns: A Survey of the Extent of User Protection", 1990, Journal of Hospital Infection, 15, pp. 375–378.

Mandlebort, et al., "A Survey of Exposure, Practices and Recommendations of Surgeons in the Care of Patients with Human Immunodeficiency Virus", 1990, Surgery—Gynecology & Obstetrics, vol. 171, No. 2, pp. 99–106.

Henderson, et al., "Risk of Occupational Transmission of Human Immunodeficiency Virus Type 1 (HIV-1) Associated with Clinical Exposures", 1990, Annals of Internal Medicine, vol. 113, pp. 740–746.

Beekmann, et al., "Risky Business: Using Necessarily Imprecise Casualty Counts to Estimate Occupational Risks for HIV–1 Infection", 1990, Infection Control Hospital Epidemiology, 11[7], pp. 371–379.

Bloomfield, et al., "Evaluation of Hypochlorite-Releasing Disinfectants Against the Human Immunodeficiency Virus (HIV)", 1990, Journal of Hospital Infection, 15, pp. 273–278.

Johnson, et al., "Efficacy of Glove Combinations in Reducing Cell Culture Infection After Glove Puncture With Needles Contaminated With Human Immunodeficiency Virus Type 1", 1991, Infection Control and Hospital Epidemiology, 12[7], pp. 435–438.

Panlilio, et al., "Blood Contacts During Surgical Procedures", 1991, Journal of American Medical Association, 265[12], pp. 1533–1537.

Gross, "Many Doctors Infected with AIDS Don't Follow New U.S. Guidelines", 1991, The New York Times, vol. CXL . . . No. 48,696, p. 1.

Orentlicher, "HIV–Infected Surgeons: Behringer v. Medical Center", 1991, The Journal of American Medical Associations, 266[8], pp. 1134–1137.

Zanowiak, "Skin Infections: The Role of OTC Therapy", Jun. 1991, U.S. Pharmacist pp. 40–47.

Mast, "Factors Predicting Infectivity Following Needlestick Exposure to HIV: A Invitro Model", 1991, Clinical Research, 39(1): p. 58A.

Wright, "Mechanicms of Glove Tears and Sharp Injuries Among Surgical Personnel,"1991, Journal of American Medical Association, 266(12): 1668–1671.

Boscia, Peterson, Szpalski, Panlilio & Gerberding, Letters to the Editor: "Surgery, AIDS, and Hepatitis B", 1991, Journal of American Medical Association, 266(10): 1360–1362.

Belkin, L. Apr. 7, 1992 New York Times, ppA1 & B2: "Fear of Disease Changing How Doctors Work".

Associated Press, Apr. 14, 1992 New York Times, ppC3: "Teen-Agers and AIDS: The Risk Worsens.".

Remington's Pharmaceutical Sciences, 13th Edition, 1965, pages 455–459, pp. 525–556, and pp. 1228–1252: "Suspensions", Chapter 37—Medicated Applications, and Chapter 74—Antimicrobial Drugs.

Remington's Pharmaceutical Sciences, 18th Edition, 1990, pp. 1163–1241: "Antimicrobial Drugs".

PROTECTIVE MEDICAL GLOVES AND METHODS FOR THEIR USE

FIELD OF THE INVENTION

The present invention is a flexible protective medical glove that relates to the thin-walled medical glove that doctors, health care workers and other workers can wear on one or both hands as a physical barrier form of protection; in particular the present invention is a glove containing a liquid antiseptic composition within the glove wall; the liquid antiseptic composition comprises an antiseptic in a liquid.

No useful medical glove is puncture-proof; when an individual wears a conventional medical glove, the thin glove wall can readily be punctured by an object and the hand underneath the glove may become wounded. If the object is contaminated with an infectious pathogen, then the hand and the hand wound may become contaminated and the individual may suffer a systemic pathogenic infection. A glove in accordance with the present invention can help to prevent the hand and the hand wound contamination from causing a systemic infection; such a glove is urgently needed in medical work environments harboring the AIDS virus, hepatitus B virus, and other infectious pathogens. When an object punctures a glove in accordance with the present invention, the object can become coated with the liquid antiseptic composition. If the object in the process causes a hand wound, some liquid antiseptic composition can be carried into the hand wound; useful as an immediate liquid antiseptic composition treatment of the contaminated hand and hand wound. Once punctured, the glove wall can also leak the liquid antiseptic composition onto the hand and into the hand wound as an means for the treatment. In addition, the gloved hand can be immediately massaged to redistribute the liquid antiseptic composition in the glove wall towards the puncture hole in the glove, to increase the rate of liquid antiseptic composition leakage.

BACKGROUND OF THE INVENTION

In general, disposible latex gloves are worn during a medical procedure to provide a physical barrier between a patient's body or tissues and the hands and wrists of a health care practicioner such as a physician, nurse, phlebotomist and the like. The gloves need to be flexible so that the manual dexterity of the health care practicioner or worker is not significantly decreased. The gloves are well-fitting and are comfortable so that glove wear does not cause hand fatigue or discomfort.

Sterile and nonsterile latex medical gloves are available. Sterile latex medical gloves are also known in the field as surgical gloves; they are sterilized at the glove factory; are made available typically as a pair in a specific size and are sealed in a sterile package. Surgical gloves are most often used for sterile field surgery to prevent a transfer of an infectious pathogen to a surface of a surgical wound from a surgeon's hands. Nonsterile latex medical gloves are also known in the field as examination gloves; they are used during non-sterile procedures; are made available usually in a size that can suitably fit either hand and are often packaged in bulk, for example in quanities of 50 per box. Non-sterile procedures include the medical examination of human body surfaces, body invaginations and body orifaces; nonsterile medical gloves are also worn for protecting the hands of medical, research or hospital workers from contact with biohazardous substances and surfaces which include but are not limited to the following: biological waste products such as feces and urine, soiled wound dressings, garments or other materials, irritating or toxic liquids or chemicals, biological toxins, radioactive substances, and infectious pathogens. For the present invention, the term "infectious pathogens" is meant to include but is not limited to the following: viruses, bacteria, fungi, rickettsia, prions, multicellular parasites, the spores of infectious pathogens, and the like.

At least three kinds of glove wall failure are known currently plague the currently known types of medical gloves. First, about two percent of standard latex gloves have inherent microscopic perforations from manufacturing that can be permeated by the smaller infectious pathogens such viruses. Secondly, during their use, medical gloves may acquire small tears, perforations or punctures which go unnoticed and provide a means for infectious pathogens, particularily in bloody contaminated body fluids, to come into contact with the hands of the glove wearer. If an infectious pathogen contacts human skin, the individual may eventually become systemically infected with the pathogen. Thirdly, a gloved hand may become contaminated with an infectious pathogen if the glove is accidentally punctured by an object that is contaminated with an infectious pathogen. The glove puncturing object may have a sharp edge like a hypodermic needle, suture needle, or scapel blade or may only have blunt edges. Clearly the currently available medical gloves are not designed to protect a hand from becoming contaminated with an infectious pathogen once the glove wall has become damaged. The breakdown of the physical barrier protection of a glove leaves a hand susceptible to contamination and infection with an infectious pathogen, and ultimately susceptible to a systemic infection with the pathogen which may have devastating consequences.

The recent emergence of several lethal vital diseases caused by infectious pathogens has created an urgent need for more protective medical gloves that retain their medical utility. Currently, the most feared infectious pathogen is the human immunodeficiency virus (HIV); this infectious pathogen is believed to systemically infect and compromise the human immune system and thereby cause Acquired Immune Deficiency Syndrome (AIDS); AIDS generally is ultimately fatal. Hepatitis B virus is another example of a lethal virus that infects humans.

Medical gloves are commonly made from elastomeric or plastic materials such as latex rubber or plastic. Materials for a glove may also be obtained from a plant fiber such as cotton, animal secretion such as silk, animal tissue such as the skin or intestine, a mineral fiber or a metal fiber. The material(s) used to manufacture a medical glove should be flexible and should be capable of being made into a fiber or a thin sheet.

A second pair of gloves may be worn over the first pair of gloves to increase the thickness of their physical barrier protection. Multiple pairs of medical gloves can be worn provided that fine dexterous hand work can still be done. If two or more pairs of gloves are worn, the medical work by the gloved hand may become difficult and tiring.

Thick-walled work gloves have been made from the same materials used to make thin-walled gloves. Thick-walled gloves are inflexible and this property has generally limited their utility to most medical doctors, health care workers, skilled workers and like workers. A number of thick-walled work gloves have been developed to protect a hand from a serious cut or puncture wound by an object. For example, thick-walled cut-resistant gloves have been developed to protect the hands in animal slaughter houses where meat is manually cut (See U.S Pat. No. 4,526,828 and PCT WO 91/10409). However, a puncture-resistant glove has not been developed that is also flexible enough for medical personnel and the like.

A glove in accordance with the present invention is designed to be thin-walled and flexible, to be comfortably worn and easily used by medical personnel and the like workers; consequently a glove in accordance with the present invention is Just as capable as a standard medical glove of being punctured by an object. But the present invention has important, novel additional functions. A glove in accordance with the present invention can immediately begin to help to protect a hand and a hand wound beneath the glove from becoming infected with an infectious pathogen after an object contaminated with an infectious pathogen has punctured the glove.

A recent study of accidental blood contact during hospital surgical procedures in burn, trauma, orthopedic, general, gynecology, and plastic surgical services concluded that surgical gloves are an important means for preventing a substantial percentage of the blood contacts with the hands (Panlilo et al, 1991). Blood and body fluids can be contaminated with infectious pathogens such as the human immunodeficiency virus (HIV, also commonly called the AIDS virus) and the Hepatitis B virus. Because many substances or material objects can temporarily harbor an infectious pathogen, medical workers are well-schooled in the risks of becoming contaminated from contacting soiled objects and body fluids from infected individuals. Medical workers are advised to wear medical gloves in any environment which may contain infectious pathogens (Panlilo et al., 1991).

The United States Center For Disease Control (U.S. CDC) has issued guidelines for the prevention and control of nosocomial infections, for hospital environment control, and for control of surgical wound infections (See publications by Simmons, B. P., 1983). The U.S. CDC reported that a clean wound (a wound that is initially pathogen-free) has only a 1 to 5 percent average risk of becoming infected; the U.S. CDC reported that a contaminated wound (a wound exposed to an infectious pathogen) has a 15 to 17 percent average risk of becoming infected, and that a dirty wound (a wound exposed to biological or environmental liquid and solid waste which may be contaminated with an infectious pathogen) has more than a 27 percent average risk of becoming infected. Therefore, an infection is more likely to occur in a dirty or contaminated wound than in a clean wound. Surgeons have administered an antiseptic solution directly into a wound as an irrigation solution (See also Maki, D. C, 1976). Furthermore the U.S. CDC guidelines have advised doctors and health care workers to wash their hands with an antiseptic detergent to reduce the microbial (infectious pathogen) contamination on their hands before they wear medical gloves. Wound cleaning and antiseptic decontamination of the hands are thus established methods for decreasing the risk of infection in a wound. The U.S. CDC has also reported that antiseptics are more effective antimicrobial agents than soap and water, but has pointed out that frequent skin contact with an antiseptic can be more irritating than soap and water to the skin.

In 1987, the U.S. CDC issued the recommendation that medical examination gloves be worn as a "universal precaution". To adhere to the universal precaution guidelines, doctors and other medical personnel are expected: (1) to assume that each patient is infected with human immunodeficiency virus (HIV) and thus to wear a new pair of gloves with each new patient, and (2) to remove their gloves and to wash their hands immediately if their hands appear to have become contaminated with blood or other body fluids (See Bartlett, J. G., 1988).

Although medical workers are well aware of the utility of an antiseptic in the prevention of skin infection and wound infection, medical glove wearers may not always be able to comply with the proposed U.S. CDC guidelines in a competent manner. It may be inconvient or impossible for a glove wearer to immediately remove a damaged or contaminated glove during surgery or during a stressful medical emergency. Such a delay in glove removal may be dangerous for the glove wearer. The time delay may permit the blood circulation of the glove wearer to become more contaminated with an infectious pathogen. Later attempts to disinfect the hand or hand wound with an antiseptic would then be ineffective in preventing the systemic infection of the individual with the infectious pathogen. The individual may also delay glove removal and cleaning the contaminated hand or hand wound with an antiseptic because the accident went unnoticed; the pain of the wound pain may not be not felt and/or hand wound bleeding may be minor or not seen. Thus, delayed glove removal and delayed hand disinfection wearer can have serious consequences.

There has been an obvious increase in the wearing of medical gloves in many health care work environments following adoption of the "universal precautions" guidelines and the epidemic growth of AIDS in the human population. To be safe, because it is not known for certainty exactly which work environments can harbor an infectious pathogen such as HIV, medical gloves are now routinely worn by many medical or public workers when they feel they are at some risk of accidental infection. The work environments or forms of work may include but are not limited to the following examples: hospitals, medical clinics, private doctor offices, emergency medical ambulance work, fire rescue work, medical practice areas involving AIDS patient care, surgery, gynecology, human fertility work, urology, general medicine, pathology, epidemiology, microbiology, neurology, orthopedics, radiology, oncology, nursing, dentistry, podiatry, psychiatry, psychiatric hospitals, hospices, other medical practices and specialties, kidney dialysis centers, diagnostic medical imaging-testing and operations facilities, hospital emergency waiting rooms, emergency hospital ambulatory care, clinics for drug rehabilitation, donor organ and tissue preservation banks and labs, blood banks, blood testing and related analytical chemistry labs, sperm banks, sperm testing labs, basic and clinical medical research labs, medical instrument cleaning, sharpening and repair facilities, hospital patient rooms, operating rooms, cleaning and maintenance work, hospital laundaries, hospital cafeterias, other hospital patient food service work, hospital morgues, funeral homes and related work areas dealing with study and handling of dead human bodies and tissues, medical and public waste or refuse collection areas, disposal areas and containers for human blood and disposible medical utensils, work with blood products, urine products or other body products, hospital trash and other disposible waste areas which might contain medical waste, work with sharp contaminated objects such as needles, syringes, wires, catheters, and intravenous sets, plastic and glass tubes and pipettes, glass slides, scalpel blades, and the like; disposible medical instruments and work areas involved in surgical instrument handling, repair and cleaning, clothing and medical assist areas; areas of medical garbage removal and medical sanitation work, medical work in retirement homes, and cleaning or industrial operations in any building where there may be any risk of a pathogenic infection. Surgical gloves and/or examination gloves (medical gloves) may be used in animal medicine and during general work with animals in research, on farms or ranchs with animals, in veterinary and animal husbandry practices and pet stores, in work with zoo animals, and in similar work where there may be some risk of contact with an infectious pathogen. Medical gloves may also provide useful protection from physical contact with infectious pathogens that may exist in potentially infectious nonmedical technical areas, scientific areas and other work areas including the following: industrial, military, or other research work that involves work with pathogens in molecular biology or molecular genetics, fermentation and vaccine production; the facilitites include any government, military, commercial, industrial, or biotechnological production, research and testing areas. Medical gloves are also useful protective hand wear in areas or in work which may include the following: public and business building maintenance work and cleaning, outdoor public areas work, restaurant work, sports clubs, spas, health clubs, massage palors, ghetto area building rehabilitation and clean-up work; guard work in jails, prisons, and other crimminal confinement facilities. Public or private vehicles used to provide surface, underground, water, underwater, air, aerospace or even outer space transport conceivably may harbor infectious pathogens. Travel in such vehicles may require an individual to wear protective medical gloves.

Conventional medical gloves are often worn to protect the hands of an individual from coming into physical contact with an infectious pathogen that infects another individual. The following individuals at risk of being infected with an infectious pathogen are listed here as a nonlimiting example: a person infected with the AIDS virus, a person infected with hepatitus B virus or other viruses, a person with a bacterial infection, a hospital patient, a health care patient, an intravenous drug user, a prostitute, a gang member, a homeless person, a mentally-ill person, a person suspected of or engaged in criminal activity, a captured or convicted or imprisoned crimminal; an illegal immigrant, an immigrant from an AIDS infested population, a new immigrant, a homosexual or bisexual individual, a sexually promiscuous individual, and a chronically-ill, elderly or incapacitated person who is at an increased risk of harboring an infectious pathogen.

A glove in accordance with the present invention may also usefully protect an individual under other circumstances. Animals, plants, soil, water, the air, and various forms of environmental pollution are capable of supporting colonies of infectious pathogens which may infect an individual. Thus workers in many nonmedical environments can also be contaminated by an infectious pathogen; such nonmedical workers include but are not limited to the following workers: law enforcement workers, police, state trooper, national guard, military personnel, traffic police, transit police, jail and prison workers, park workers and park cleaners, sanitation workers, city morgue workers, hospital morgue workers, funeral home workers, and cemetary workers, waste and water treatment facility workers, street cleaners, sewer workers and other municipal workers, persons cleaning public bathrooms and portable toilet maintainance workers.

In addition, gloves in accordance with the present invention can be worn by any doctor, dentist, health care worker and the like or other individual who choses to continue working after they have tested seropositive with an infectious pathogen such as HIV or hepatitus B virus (See News York Times article by Jane Gross, dated Aug. 18, 1991). It is particularly important for infected medical personnel to wear protective medical gloves so that they do not transmit their infection via their hands to another person.

If an object cuts, or otherise penetrates a thin medical glove wall while it is being worn on a hand, the physical barrier protection provided by the glove is immediately lost. Such an accident to a glove may in the process also wound the hand and this wounding can expose the blood circulation of the individual to an infectious pathogen; becoming wounded is particularly traumatic if the surface of the wounding object is thought to be contaminated with an infectious pathogen such as HIV.

Medical personnel in particular know that a conventional medical glove can not adequately protect the hand it covers from a hand-wounding accident with an AIDS-contaminated object such as a syringe needle. A variety of medical objects have caused an instant HIV inoculation to the hands of health care workers wearing standard surgical or examination gloves (See Henderson et al., 1990; Beekman et al., 1990; Panlilo et al., 1991).

For the present invention, the term glove wall puncture is defined broadly to encompass glove wall punctures caused by any process. A glove wall puncture may be caused by any physical object capable of cutting, biting, abrading, puncturing, stabbing, crushing, or otherwise physically penetrating the glove wall. When such objects are contaminated with an infectious pathogen, they can act as a carrier for the transfer of the infectious pathogen to the hand and the hand wound. Alternatively, the glove wall puncture may be caused in the absence of a solid physical object, by one or more of the following processes: a chemical reaction with the glove, a solvent that can dissolve the glove wall, a change in the ambient gas pressure or liquid pressure over the glove wall, a powerful electrical shock through the glove wall, a thermal melting or burning of the glove wall or a low temperature fragmentation of the glove wall; in these examples, the process causing the glove wall puncture may not act as a carrier for the transfer of an infectious pathogen to the hand or the hand wound. In general however, a glove wall puncture creates the access means for an infectious pathogen to contact the hand or a hand wound from the exterior surface of the glove.

Health care workers and medical doctors in particular, know that hand wounding is a common accident that they often experience a number of times each year in their work environments because conventional medical gloves are not puncture-resistant (Panlilio et al., 1991; see especially Wright et al., 1991). For the present invention, the term "hand" is herein broadly defined to encompass all portions of an arm and a hand that may be covered by a glove in accordance with the present invention; thus use of the term "hand" may refer to the fingers, all surfaces of the hand, the wrist, the forearm, and may refer even to the surfaces of the arm up to the armpit and shoulder for some embodiments of the present invention.

Health care workers and other professionals who care for patients with AIDS know that they can become infected with the AIDS virus (HIV) from the AIDS patients. It is important to consider that as a result of the AIDS epidemic, medical doctors and health care workers now work with increased anxiety and fear of contracting AIDS; that an accidental hand wound during their professional work may infect them with HIV and shorten their lives (Gerberding and Schecter, 1991). Each time a gloved hand is wounded by an object contaminated with blood or other body fluids, the wounded medical worker must psychologically deal with the possibility that the wound was contaminated with HIV, that the medical worker may be at risk of a systemic HIV infection. Thus, there is a particularily urgent need for an improved medical glove that can better protect a hand when the hand is wounded by an object that may be contaminated with an infectious pathogen such as HIV.

Some medical doctors and health care workers have been reluctant to admit that they have obtained a hand wound during their work from an object possibly contaminated with HIV or that their blood has tested positive for HIV antibodies because this information may indicate that they may have a systemic HIV infection. Such disclosures can threaten their employment in health care (See Orentlicher, D., 1991; and New York Times article by Jane Gross, dated Aug. 18, 1991). As a result of the unreported HIV infections, the data gathered to estimate the incidence of accidental skin punctures among health care workers is undoubtedly underestimated and thus inaccurate.

As already mentioned, sharp medical instruments and needles in use by medical personnel can easily puncture a standard medical glove on a hand and the hand underneath the glove can become wounded (See Gerberding and Schecter, 1991). The reported incidence of accidental skin punctures to hospital surgical personnel in three major municipal hospitals (in San Francisco, Albuerque, and Atlanta) has averaged 2 to 5 injuries per 100 procedures (Panlilio et al., 1991; Gerberding et al., 1990; Gerberding and Schecter, 1991). These hospitals have also reported that occupational exposure to blood occurred often in surgical settings (Gerberding et al., 1990; Gerberding and Schecter, 1991; Panlilio et al., 1991). Accidental blood contact between a patient having HIV and workers in other more casual (nonsurgical) medical settings has been predicted to increase in view of the epidemic spread of HIV infection in the United States and in the World (Gerberding et al., 1990).

Three known factors that can affect the risk of a medical worker becoming infected with an infectious pathogen are (1) the prevalence of blood-borne infection in the patient population under treatment by the medical worker, (2) the frequency and types of hazardous exposure that the medical worker is subjected to, and (3) the risk of infection that accompanies each exposure to the medical worker (Gerberding and Schecter, 1991). It thought unlikely that medical personnel can control the first two factors and still remain valid health care workers. It is an object of the present invention to lower the worker's risk from the third factor, namely a glove in accordance with the present invention can lower the risk of infection that accompanies each hazardous exposure to a medical worker's hand.

The risk of systemic HIV infection to an individual wounded on a hand from a single hollow needle stick has recently been estimated to average roughly 0.4 percent (1 occurence in 250 events). This risk estimate was calculated from observations of documented needlestick wounds that were contaminated with blood from patients having an advanced stage of HIV infection during which their blood had an elevated HIV titer (Beekman et al., 1990; Henderson et al., 1990). This estimate is obviously an underestimate because some hand injuries will not be reported and therefore this study underscores the real risk medical workers experience.

Analysis of the risk of infection that accompanies each individual exposure of the hand and the hand wound to an infectious pathogen has been conducted, based upon an in vitro study of glove wall punctures by needles. The study found that the risk was influenced by several variables. An important variable was the volume of infectious blood transferred by the needlestick (See Mast and Gerberding, 1991). Other important variables included (1) the titer of the infectious pathogen in the contaminating blood, (2) the needle type and size, and (3) the depth of skin penetration by the pathogen contaminated object. Other observations have shown that wearing a standard medical glove on the hand can reduce the volume of blood transferred to the hand wound by about 50 percent (See Gerberding and Schecter, 1991). When two pairs of standard medical gloves were worn on the hand, the contamination of the hand wound by blood was further reduced to between 20 to 40 percent, (Gerberding and Schecter, 1991; Mandelbrot et al., 1990). Thus, studies have found that wearing two gloves on a hand can not adequately protect a hand, as it is wounded by a blood-tainted needle, from becoming contaminated with a substantial fraction of the foreign blood, infectious pathogens or other substances present on the blood-tainted needle. In view of the (a) marginal protection that conventional gloves can provide, (b) the frequency of accidental hand wounds by gloved health care workers, and (c) the increasing incidence of HIV infection in the human population, it is reasonable to expect that the probability of any health care worker becoming infected with HIV during work as a result of HIV contamination of a hand wound will increase. Because almost every HIV infection eventually causes AIDS which is believed to be fatal for almost all individuals, the medical profession is greatly concerned that the risk of HIV infection from a medical glove puncture is too high and urgently needs to be substantially reduced (See Orentlicher, 1991).

A glove capable of providing an immediate liquid antiseptic composition treatment to a hand or a hand wound would be a novel invention. The prior art has not disclosed a glove having a wall storing or leaking a liquid antiseptic composition which comprises an antiseptic in a liquid. The prior art has not disclosed the use of a glove capable of storing a liquid antiseptic composition or capable of leaking the liquid antiseptic composition onto a hand or into a hand wound as a treatment means for the hand and the hand wound when the glove is punctured and/or the hand is wounded by an object that may be contaminated with an infectious pathogen. To have medical utility, such a protective medical glove would need to retain the flexibility and the comfortability characteristics of conventional medical gloves. A glove in accordance with the present invention can meet these requirements but has not been identically disclosed or described in the prior art. Related prior art is described below but is not identical to the present invention. In view of the prior art, the subject matter of the present invention as a whole would not be obvious to persons of ordinary skill in the art pertaining to the subject matter of the present invention at the time of the invention.

A protective gel composition has been disclosed (U.S. Pat. No. 5,019,604 issued May 28, 1990 to G. M. Lemole) for coating the skin prior to covering the hands with standard surgical gloves. In one example, the composition contains lanolin, liquid silicone, polypropylene glycol monoleate, polytetrafluoroethylene powder in microspherical form, zinc oxide powder, anti-bacterial agents and antiviral agents with a preferred agent being nonoxynol-9. The composition forms a water repellent coating on the skin to prevent the skin contacting body fluids such as blood and blood products that may penetrate the gloves and otherwise expose the skin to harmful microbial and vital infections. The use of a protective gel to continuously contact the skin with chemicals may be irritating to the hands. After glove removal, the gel coating the skin must be washed off. Some individuals may also find that the number of step required to use and remove the gel is disagreeable. Use of the gel composition in a liquid composition in between two gloves was not suggested.

Use of antiseptic-coated gloves has been disclosed in a study of surgical hand hygiene (*J. Hospit. Infect.* 1988, 11 Supp. A:244-250 by Newsom et al.). Gloves were coated with solid cetylpyridinium chloride and surpressed skin flora counts after prolonged operations in comparison to standard gloves, but the solid antiseptic coating may cause hand irritation after prolonged contact. Use of such antiseptic in a liquid composition in between two gloves was not suggested.

Use of the antiseptic 4.0% chlorhexidine gluconate detergent formulation containing 4.0% isopropyl alcohol (Hibiclens/Hibiscrub) and the antiseptic 0.50% chlorohexidine gluconate in 70.0% isopropyl alcohol with emollients (Hibistat/Hibisol) as a skin treatment has been disclosed (*J. Hospital Infection,* 1990, 15:279-282 by Montefiori DC et al.). This antiseptic composition was found to inactivate HIV in experimental cell cultures after 15 seconds when used at 1:100 and 1:5 dilutions. Use of such antiseptic in liquid composition in between two gloves was not suggested.

A sterile glove has been disclosed in which the antibacterial agent zeolite is immobilized in a plastic film on one or both surfaces of the glove; useful for handling food, for work in a kitchen or for medical purposes (U.S. Pat. No. 5,003,638 issued Apr. 2, 1991 by T. Miyake and T. Yamamoto). According to the Merck Index (8th Edition), zeolite is a hydrated dust or powder of alkali aluminum silicate. An immobilized thin layer of antibacterial agent can not help to prevent a hand wound infection. Use of such antiseptic in liquid composition in between two gloves was not suggested.

A glove has been disclosed which was made by first immobilizing an anti-microbial agent into rubber and by then solidifying the mixture into a glove (U.S. Pat. No. 5,031,245, issued Jul. 16, 1991 by Milner, R.). The glove was reported to be an improved barrier to HIV. A non-ionic, sparingly water-soluble antimicrobial agent that does not coagulate natural rubber latex such as chlorophene, dichloroxylenol, hexachloraphane was used; diphenyl derivatives may be halogenated and used such as 0.1% to 10% by wt. 2,4,4'-trichloro-2'-hydroxyphenyl ether, diacetylaminoazotoluene, triclocarban and triclosan. The surface of the glove was dusted with a powder containing an antimicrobial agent such as chlorhexidine digluconate and cyclodextrin. The antiseptic dust on the glove surface contacts the hand while the glove is worn and may irritate the skin. Use of such antiseptic in liquid composition in between two gloves was not suggested.

A multilaminar hybrid glove has been disclosed having at least an outer rubber layer, an inner rubber layer and at least one intermediate cotton material layer impregnated with a gel containing nonoxynol-9; regions of the glove may be protected with an armor of fungicide-coated, puncture-resistant Kevlar plastic (*Infect. Control Hospital Epidemiol.* 1991 12(7): 435-438 by Johnson et al., 1991). In vitro tests found that the glove with Kevlar resisted some needlestick punctures. In vitro tests found that the glove reduced the transfer of HIV from a solid needle tip to a culture dish by chemical inactivation of the virus on the needle when the needle contacted the gel containing nonoxynol-9 in the cotton layer. Results using "hollow" syringe needles were not obtained and the authors indicated they could not predict such results without additional study. The multilaminar glove was stiff and thick walled, and therefore was useless as a flexible protective glove for a hand that had to be able to comfortably perform medical tasks. The use of nonoxynol-9 in a liquid composition stored between two medical gloves was not suggested.

The present invention is directed to providing novel protective glove designs and methods for their use. A glove in accordance with the present invention contains within its glove walls a liquid antiseptic composition which comprises an antiseptic in a liquid. The subject matter of this invention as a whole has not been made obvious nor was it suggested by either the prior art concerning protective medical gloves or the prior art concerning protective antiseptic compositions for the hands. The flexible protective medical gloves which comprise the present invention solve the problem of protecting a gloved hand from an infection when the glove is punctured and the hand underneath the glove is wounded by an object contaminated with an infectious pathogen. The method of using the present glove invention is simple because the substantial protective functions of the glove are semi-automated; thus the present invention is an important advancement in the medical glove field because the a glove in accordance with the present invention can help to immediately treat an infectious pathogen contaminated hand and hand wound with a liquid antiseptic composition provided that the contamination has arisen from the act of a glove puncturing object while the glove is being worn. A further advantage of the present invention over the prior art is that contact and thus unnecessary irritation of the hand by the antiseptic composition is avoided until the glove wall is punctured by an object.

SUMMARY OF THE INVENTION

It is an object of the present invention to provide a flexible protective medical glove having a thin glove wall comprising at least an outer glove layer of a first material having a thickness of between about 1 mil (1 mil is one-thousandth of an inch) to about 40 mils and at least an inner glove layer of a second material having a thickness of between about 0.3 mils to about 30 mils wherein the first material and the second material form at least the walls of a compartment storing a liquid antiseptic composition. The compartment storing the liquid antiseptic composition generally has a thickness ranging between about 10 mils to about 100 mils, but in some areas of the glove, particularily while the glove is being worn, it is imagined that the compartment could become temporarily compressed to less than 1 mil in thickness; alternatively or at the same time the compartment in some areas of the glove may be expanded by design or while the glove is being worn could become temporarily expanded to a thickness exceeding 500 mils. At the end of the glove where the hands would be first inserted, the compartment may be open or may be closed. Alternatively, the glove may be capable of being reversibly opened or closed using for example a ziplock or sealing seam between the glove layers at the opening of the compartment, to allow the individual that wears the glove to increase or reduce the amount of liquid antiseptic composition in the glove. Preferably the compartment is closed. A glove in accordance with the present invention can be as flexible a conventional medical glove; this is needed to permit the gloved hand to easily and adequately perform delicate, dexterous and complex hand work including for example, the hand work of a surgeon, a medical doctor, a dentist, a laboratory worker, a health care worker, a law enforcement worker, a hospital worker and like workers. It is conceivable that the glove wall can be constructed from almost any material or combination of materials provided that at least the surface of the inner glove layer and at least the surface of the outer glove layer are liquid-impermeable. Most preferably the glove wall layers are made using thin flexible layers of rubber and/or plastic materials.

The liquid antiseptic composition comprises an antiseptic in a liquid. Preferably the liquid antiseptic composition contains at least one of the following antiseptics: povidone-iodine, elemental iodine, sodium iodide, potassium iodide, sodium hypochlorite, nonoxynol-9, and chlorhexidine gluconate in a liquid such as ethanol, water, isopropanol, or a mixture of the liquids thereof. Preferably the liquid antiseptic composition further includes at least one surface active agent. The liquid antiseptic composition may also contain one or more of the following substances: an organic silicone, an organic solvent, a salt, an acid, a base, a pH buffer, a preservative that can help to stabilize the antiseptic activity, a metal ion chelator, a sticky chemical additive or a viscosity-modifying agent that can help to increase the coating of the glove puncturing object with the liquid antiseptic composition, a chemical scent that can help to increase the smell or render the odor of the liquid antiseptic composition more pleasant, an emulsifier and/or a foaming agent that can help to better mix the liquid antiseptic composition with the contaminants on the hand and in the hand wound containing infectious pathogen, glycerin, a soap, a detergent, an algesic agent (a pain-causing agent), a coloring agent, or a vasoconstricting agent.

The present invention also provides a new method of protecting a gloved hand from an infectious pathogen in the event of glove damage while the glove is being worn.

It is another object of the present invention to also provide methods for the use of the present invention. Gloves in accordance with the present invention, like standard medical gloves, can provide a useful thin physical barrier form of protection to the hands. It an object of the present invention to minimize contact between the hand and the liquid antiseptic composition to reduce unnessary irritation of the hand by the antiseptic until such time that the wall of the glove is punctured by an object, and the antiseptic must contact the hand. When an object punctures the thin walls of the glove, it is an important object of the present invention to immediately begin to treat the hand and the hand wound should the wound occur, with a liquid antiseptic composition.

The treatment of liquid antiseptic composition from the glove should be capable of inactivating, killing, and/or otherwise destroying the infectious pathogen that the liquid antiseptic composition may contact. The liquid antiseptic composition should be capable of disabling the contacted infectious pathogen so that the infectious pathogen is no longer dangerous to the hand and the hand wound of the contaminated individual. For the present invention, the term "infectious pathogen" has a broad meaning intended to encompass known and yet to be discovered pathogenic microorganisms including prions and viruses as well as the biochemical cofactors or molecular fragments that can be synthesized or released by an infectious pathogen or other biological cells or may arise by other biosynthetic means; the term is intended to include biochemical cofactors and chemical fragments including but not limited to the following: deoxyribonucleic acids (DNA), ribonucleic acids (RNA, mRNA, tRNA and the like), protein cofactors, and the enzymes that act upon DNA, RNA, mRNA, tRNA and like nucleic acids in any form or conformation which may alter the potency of a pathogenic infection. The nonhuman proteins that help HIV to inhibit the human immune system are considered to be protein cofactors and fall under the term infectious pathogen as it is employed by the present invention. Some of these proteins may affect the binding of HIV to human cells. Damage to these proteins by the liquid antiseptic composition can have an anti-infective utility. Thus, the term "infectious pathogen" for the present invention is broadly meant to include at least the following infectious pathogens in all forms of their existence: viruses, bacteria, yeasts, molds, algae, other fungi, multicellular parasites, rickettsia, prions, the spores of infectious pathogens, and any of the biochemical molecular fragments of an infectious pathogen (i.e., DNA, the various RNA molecules, associated DNA and RNA enzymes and associated proteins) that can contribute to the infectivity of an infectious pathogen.

For some embodiments of present invention, it is an important object that the liquid antiseptic composition have potent antiviral or viricidal activity against the human immunodeficiency virus (HIV), and/or the Hepatitis B virus.

An object of the present invention is to help to protect the hand and the hand wound should the wound occur, from becoming infected by a glove puncturing object that is contaminated with an infectious pathogen. When the glove wall is punctured by an object, the object may in the process also wound the hand and come into contact with the blood circulation of the individual. In passing through the glove wall, the object can become coated with liquid antiseptic composition and can carry some liquid antiseptic composition along with the infectious pathogen contamination to the hand and into the hand wound, useful as an immediate liquid antiseptic composition treatment to the hand and the hand wound that can help to immediately protect the individual from developing a systemic infection with the infectious pathogen.

Another object of the present invention is to have the punctured glove wall leak liquid antiseptic composition from the puncture hole in the glove wall. The liquid nature of the liquid antiseptic composition is a novel and important property of the present invention. A liquid antiseptic composition can flow onto the hand and into the hand wound; useful as a means for providing a liquid antiseptic treatment to the hand and the hand wound that can begin to help to protect the individual from a systemic infection with the infectious pathogen.

In one embodiment according to the present invention, the glove is comprised of a liquid-impermeable outer layer of a first material and a liquid-impermeable inner glove layer of a second material wherein the first material and the second material form the walls of a compartment capable of containing a liquid antiseptic composition; the compartment contains or stores the liquid antiseptic composition which comprises an antiseptic in a liquid medium. The glove also has the capability to provide a coating to at least a portion of the object puncturing the glove wall; the coating comprising the liquid antiseptic composition; the coating on the object providing a means for immediately transfering some of the liquid antiseptic composition onto the hand and into the hand wound resulting from the object puncturing the glove wall while the glove is being worn; the liquid antiseptic composition transferred to the hand and the hand wound having the capability to provide an immediate liquid antiseptic composition treatment to the hand and the hand wound areas that may be contaminated with the infectious pathogen transferred from the object. The glove has the additional capability to leak some of the liquid antiseptic composition from a section of the glove wall having a hole resulting from the object puncturing the glove wall; the liquid antiseptic composition leaking from the hole having the capability of flowing onto the hand and into the hand wound as a means for providing a liquid antiseptic composition treatment to the hand and to the hand wound that may be contaminated with the infectious pathogen. The glove has the further capability of treating the hand and the hand wound with a liquid antiseptic composition when the object punctures the glove wall, when the object contacts the hand, when the object may wound the hand and when the object may contaminate the hand and the hand wound with the infectious pathogen; wherein the liquid antiseptic composition transferred from the glove to the hand and the wound on the hand can help to protect the hand, the hand wound, and the systemic circulation of an individual by killing, inactivating and/or otherwise destroying the infectious pathogen that may be contaminating the hand and the hand wound.

In a second embodiment according to the present invention, the glove contains a liquid antiseptic composition which is also capable of being redistributed within the compartment of the glove by massaging the glove to force the liquid antiseptic composition in the compartment to accumulate near the glove wall having the hole caused by the glove-puncturing object. As a result, the liquid antiseptic compostion can leak at an increased rate from the punctured glove wall having the hole onto the hand and into the hand wound; the additional liquid antiseptic composition contacting the hand and the hand wound can provide additional protection to the hand, the hand wound, and the systemic circulation of an individual from an infectious pathogen that may be contaminating the hand and the hand wound as a result of the contact of the hand and hand wound by the glove-puncturing object.

In another embodiment according to the present invention, the glove contains a liquid antiseptic composition which may also contain a pain-causing chemical such as a potassium salt, bradykinin or substance P. An object of the pain-causing chemical is to provided enhanced pain sensation at the hand wound to better warn the glove wearer that they may have suffered a hand wound.

According to another embodiment of the present invention, the glove contains a liquid antiseptic composition which may also contain a colored substance such as a dye or an opacifier to help visually signal when and where a glove wall has been punctured. It is an object of the present invention to alert and to protect the glove wearer, particularily an overly stressed glove wearer, of glove damage that might otherwise be missed.

According to another embodiment of the present invention, the glove contains a liquid antiseptic composition which may also contain a chemical capable of producing a distinctive chemical smell or odor which can be either bad smelling or pleasant smelling. Sudden release of a distinctive chemical odor from a gloved hand or glove is a useful means for increasing a glove wearer's awareness that a glove may be damaged.

According to another embodiment of the present invention, the glove contains a liquid antiseptic composition which may also contain a vasoconstricting agent; preferably a catecholamine such as epinephrine or norepinephrine. An object of the vasoconstricting agent is to constrict blood flow in the hand wound area as a means for limiting the systemic dispersion of the infectious pathogen from the hand wound by the blood circulation or by the lymphatic circulation of the gloved individual.

According to another embodiment of the present invention, the glove contains a liquid antiseptic composition which may also contain a viscosity-modifying agent to alter the physical flow properties of the liquid antiseptic composition; this additive can be particularily useful as a means for increasing the thickness of the coating of liquid antiseptic composition on the glove-puncturing object.

According to another embodiment of the present invention, the outer surface layer of the glove wall is comprised of an elastic material such as a rubber material; and the inner surface layer of the glove wall is comprised of a plastic material. After a glove puncture has occurred and the object has been removed from the glove wall, the hole in the elastic outer layer of the glove may shrink while the hole in the less-elastic inner layer of the glove is not as capable of contracting to a small size due to glove layer material properties. Thus, more liquid antiseptic composition may leak from the glove wall onto the hand and into the hand wound than from the glove wall onto the outer surface of the glove.

According to another embodiment of the present invention the glove wall has a plurality of glove layers acting as a structural connection which reconfigures the compartment storing the liquid antiseptic composition into a plurality of compartments capable of storing the liquid antiseptic composition. This can be useful as a means for selectively partitioning the liquid antiseptic composition in the glove wall.

According to another embodiment of the present invention, the glove wall comprises a sponge-like wall structure capable of acting as a structural connection which reconfigures the compartment storing the liquid antiseptic composition into a plurality of compartments capable of storing the liquid antiseptic composition; the outer and inner surfaces of the glove wall are coated with a liquid-impermeable coating of a rubber or a plastic material. The actual number of pore-sized compartments, the degree of segmentation of the glove wall into the compartments, and the volume of each subcompartment is not critical and may be highly variable.

According to another embodiment of the present invention, the compartment storing the liquid antiseptic composition is subdivided into a number of smaller compartments as a means for controlling the distribution and capacity for redistribution of the liquid antiseptic composition within the glove wall. Each smaller compartment may be connected to another small compartment by at least one hole so that liquid antiseptic composition can flow between the small compartments. Some of the subdivided compartments may be closed.

According to another embodiment of the present invention, the compartment storing the liquid antiseptic composition is subdivided into a plurality of closed compartments as a means for controlling the distribution of the liquid antiseptic composition within the glove wall.

According to another embodiment of the present invention, the compartment of the glove storing liquid antiseptic composition is connected to an additional resevoir of liquid antiseptic composition whose flow can be regulated by a one-way flow valve.

The subject matter which we regard as our invention is more particularily pointed out and distinctly claimed in the concluding portion of this specification. Other features and advantages are inherent in the protective glove and method claimed and disclosed for its use or will become apparent to those skilled in the art from the following detailed description in conjunction with the accompanying diagrammatic drawings.

DETAILED DESCRIPTION OF THE INVENTION

Figure 1A:
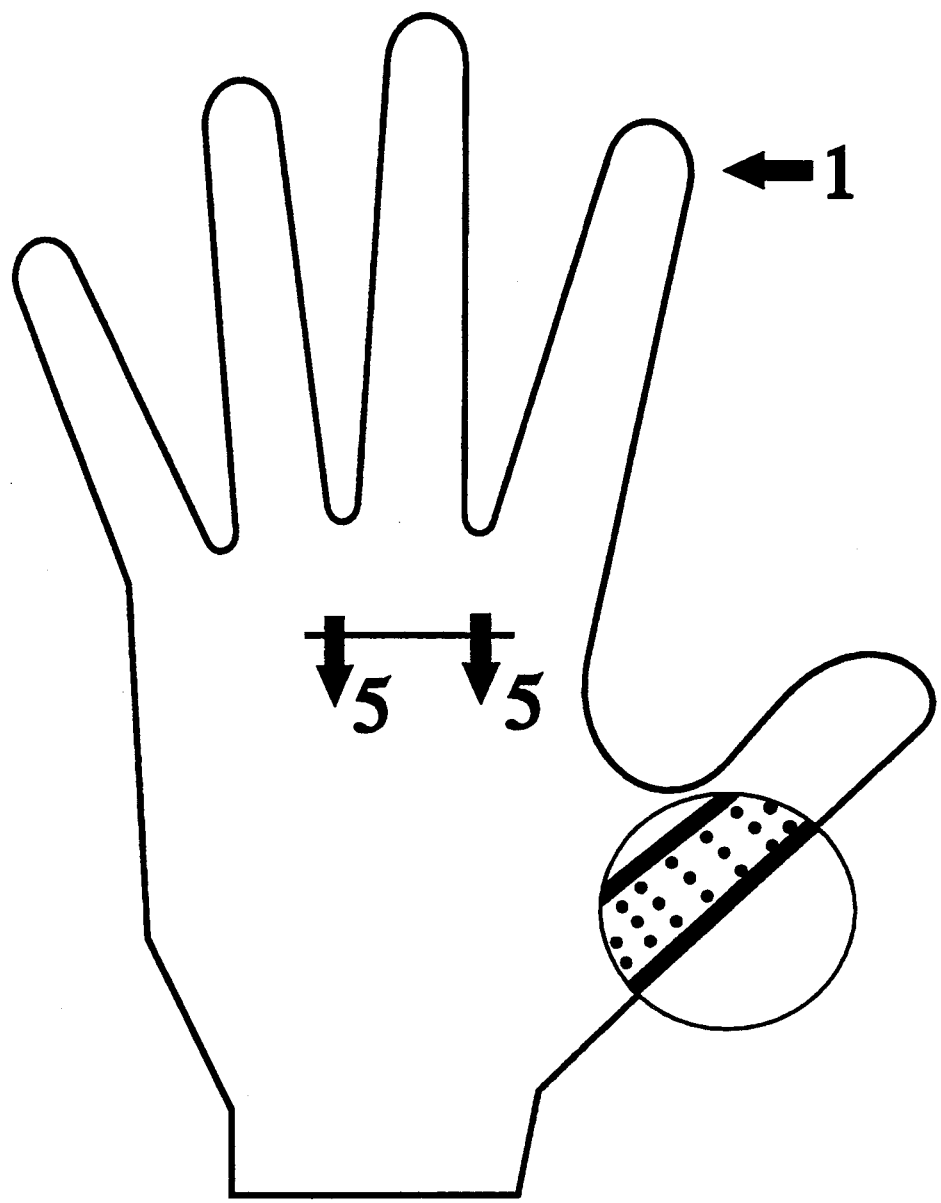
FIG. 1A is a perspective view and a partial enlarged view illustrating a glove containing a liquid antiseptic composition between an outer layer of a first material and the inner layer of a second material in accordance with the present invention.

FIG. 1A illustrates a glove in accordance with the present invention; the glove indicated generally at 1 is composed of flexible materials forming a liquid-impermeable wall having the capability to provide a liquid antiseptic composition treatment to a hand and to a hand wound underneath the glove while the glove is being worn when the wall of the glove is punctured and/or when the hand is wounded by an object that may be contaminated with an infectious pathogen.

It is an object of the present invention to provide a glove having any conceivable arm length, up to and including a glove having an arm length that can protect the entire arm of an individual up to about the shoulder region of the individual. Whereas the normal length of the glove is between about 6 inches and about 12 inches, the arm-length glove could be as long as 36 inches.

A glove in accordance with the present invention can be made sufficiently elastic so that one size glove may be worn on different sized hands; in this aspect the glove would be analogous to the conventional medical examination glove. Alternatively, a glove in accordance with the present invention can be made in different sizes so that the glove does not need to be substantially stretched and unduly stressed in order to closely fit the hand; in this respect the glove would fit the hand closely like a conventional medical surgical glove.

Figure 1B:
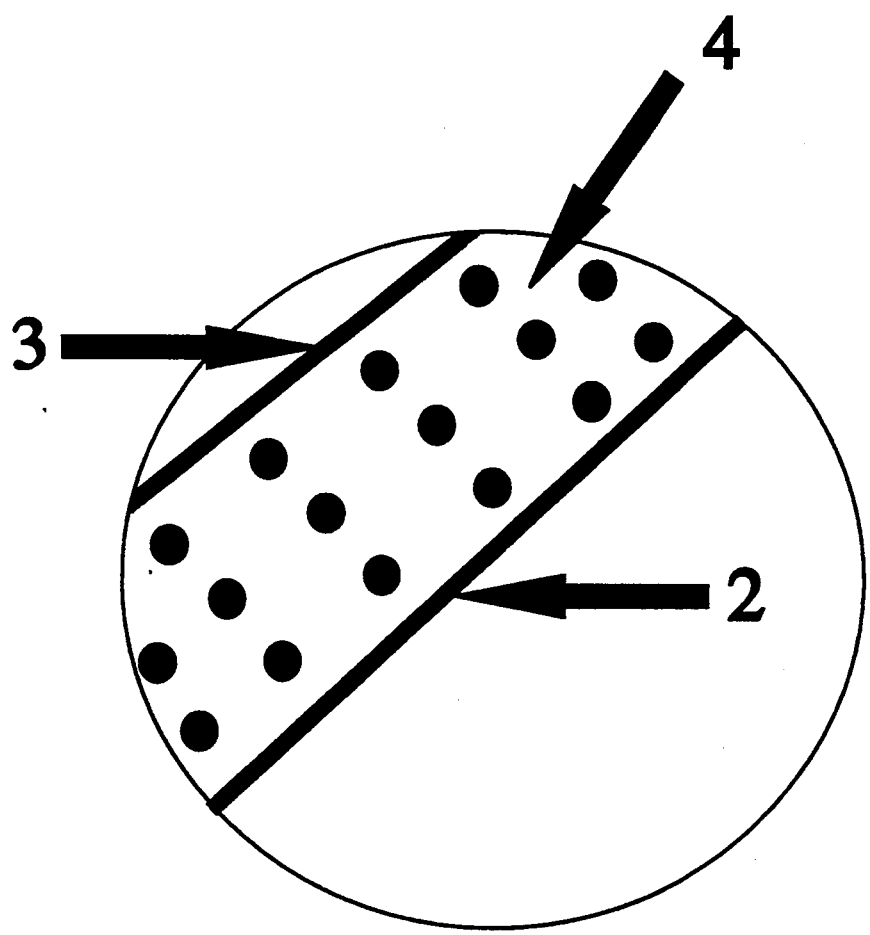
FIG. 1B is a partial enlarged view of the section of a glove wall shown circled in FIG. 1A.

FIG. 1B is an enlarged view of a representative section of the glove wall shown circled in FIG. 1A. FIG. 1B illustrates that the glove wall comprises an outer layer 2 of a first material and an inner layer 3 of a second material. The first material and the second material form the walls of a compartment 4 capable of containing or storing a liquid antiseptic composition.

A glove in accordance with the present invention contains a liquid antiseptic composition in compartment 4. Liquid antiseptic composition is symbolized in all Figures by stippling the area in the Figure with dots. The liquid antiseptic composition comprises an antiseptic in a liquid. Some antiseptics which are liquids may serve in the liquid antiseptic composition as both the antiseptic and the liquid component; an example would be the use of an alcohol.

It is another object of the present invention to provide a glove wall capable of providing a physical barrier as a means of protecting the hand while the glove is being worn by an individual. The glove provides a useful physical barrier until a portion of the glove wall is punctured by an object. When a glove in accordance with the present invention is worn on the hand of a working individual such as a surgeon, a medical doctor, health care worker, or other worker, the glove wall should be sufficiently flexible that the the gloved hand can easily and adequately perform delicate, dexterous and complex work.

It is another object of the present invention to provide the method of using a flexible protective glove with a liquid-impermeable wall on a hand of an individual to protect the hand in the event that an object contaminated with an infectious agent punctures the glove, may wound the hand and may contaminate the hand and the hand wound with the infectious pathogen, comprising the steps of:

(a) using the glove initially as a liquid-impermeable physical barrier to infect ious pathogens; using the glove to permit the hand to perform a delicate, dexterous and complex type of work that includes the type of work performed by a surgeon, a medical doctor, a dentist, a laboratory worker, a hospital health care worker, a law enforcement worker, and a hospital worker; and storing a liquid antiseptic composition in the glove wall;

(b) using the glove to coat a portion of an object puncturing the glove wall with the liquid antiseptic composition when the object punctures the compartment storing the liquid antiseptic composition;

(c) using the object puncturing the glove to transfer a portion of the coating of the liquid antiseptic composition on the object, to the hand and into the hand wound when the object contacts the hand;

(d) using the glove wall having the hole formed by the object as a means for leaking the liquid antiseptic composition onto the hand and into the hand wound; and (e) using the liquid antiseptic composition fro the glove that is on the hand and in the hand wound to kill, to inactivate, and to otherwise destroy the infectious pathogen transferred to the skin and into the hand wound by the object.

It is another object of the present invention to provide a glove that can be worn to protect an individual from an infectious pathogen; such a glove is particularily useful for a worker who ordinarily needs to wear a pair of standard medical or surgical gloves to protect their hands during their work. Gloves in accordance with the present invention can provide superior protection compared to conventional medical gloves. The present invention should be particularily useful for medical personnel such as doctors, surgeons, dentists, laboratory workers, health care workers, and other hospital workers; the gloves should be especially useful for individuals handling an AIDS infected patient or Hepatitis B infected patient.

Figure 2A:
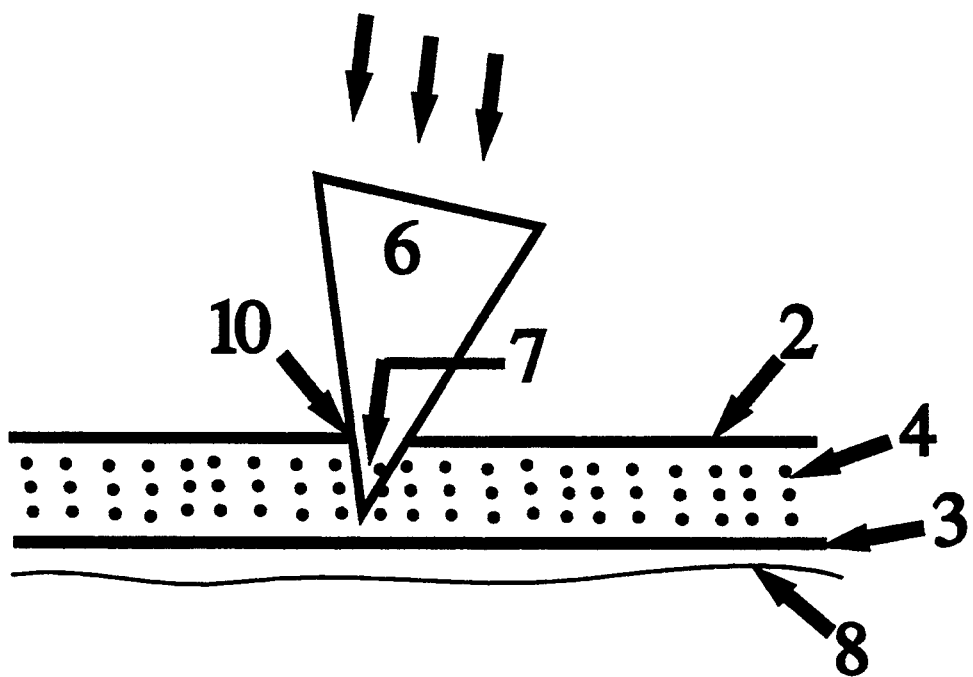
FIG. 2A is an enlarged sectional view of a glove wall taken along line 5—5 in FIG. 1A, illustrating one edge of an object which is puncturing a glove in accordance with the present invention; in this example, the object is puncturing the glove wall along Line 5—5 and the liquid antiseptic composition in the glove wall is coating the object.
Figure 2B:
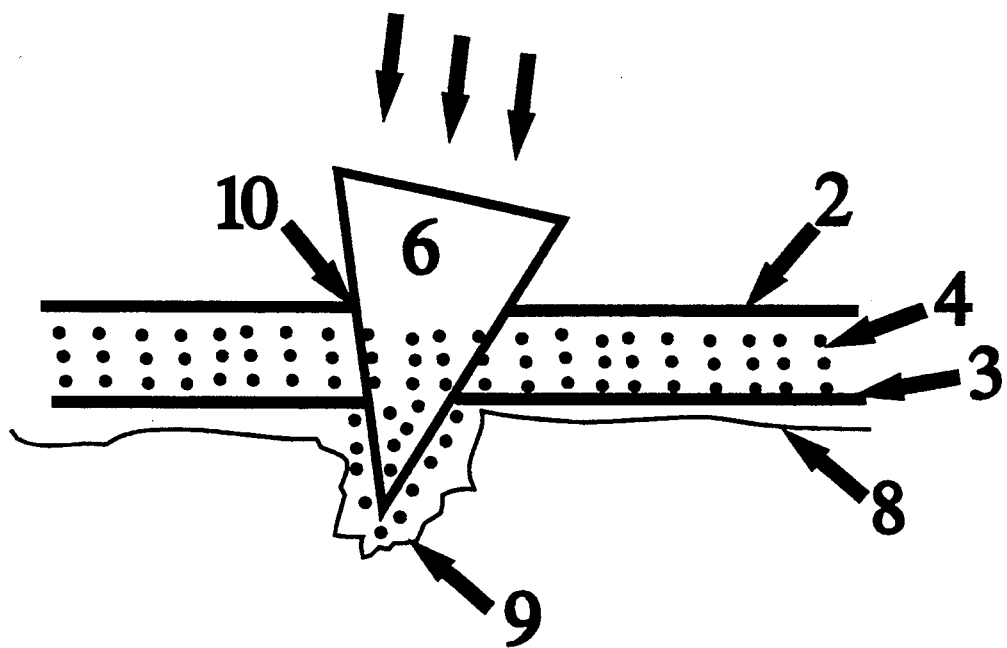
FIG. 2B illustrates the situation of FIG. 2A at a later point in time, after a portion of the object has fully punctured the glove wall and has then wounded the hand; in the process liquid antiseptic composition coating the object has been transferred to the hand and hand wound as an antiseptic treatment to the hand and to the hand wound.
Figure 2C:
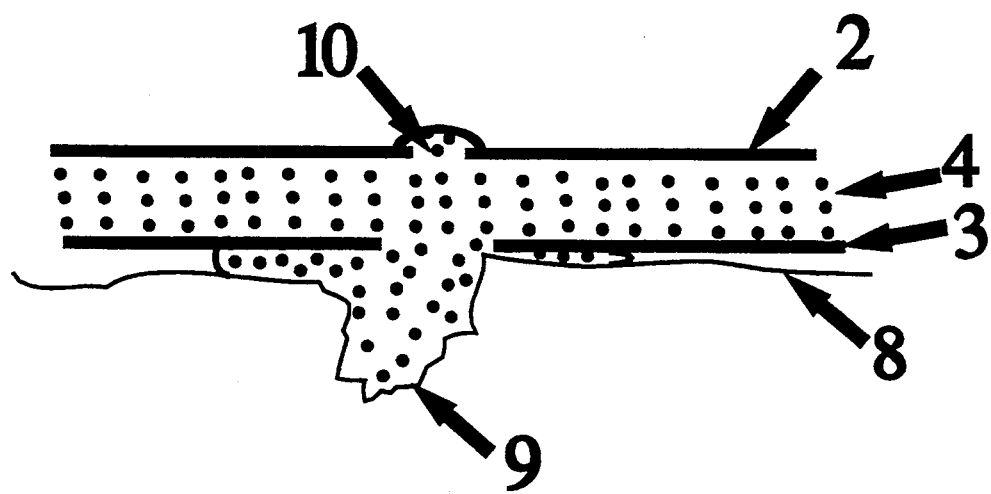
FIG. 2C illustrates the situation of FIG. 2B at a later point in time, after the object has been removed from the punctured glove; liquid antiseptic composition is leaking onto the hand and into the hand wound from the hole left in the glove wall by the object.
Figure 2D:
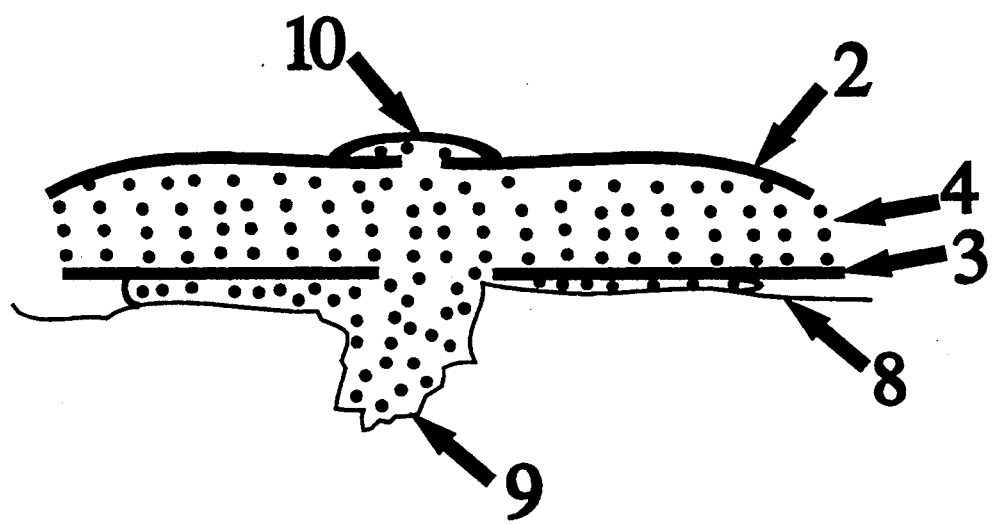
FIG. 2D illustrates the situation of FIG. 2C at a later point in time, after the damaged glove has been massaged; the massage causing increased liquid antiseptic composition to accumulate in the glove wall near the hole in the glove, the accumulation increasing the leak of liquid antiseptic composition from the glove hole to the hand and the hand wound.

FIG. 2A, FIG. 2B, FIG. 2C, and FIG. 2D illustrate another object of the present invention: how the glove can function during an accidental glove puncture by an object while the glove is being worn on a hand. Like a standard medical examination glove or surgical glove, a glove in accordance with the present invention is thin-walled and is capable of being punctured by an object if adequate force is applied by the object against the glove wall. For the present invention, the definition of a glove-puncturing object includes objects capable of puncturing, tearing, penetrating, cutting, abrading, shredding, biting, or otherwise disrupting the physical integrity of the glove wall to such a degree that a portion of the glove wall is no longer liquid-impermeable. As mentioned already, the wounding of a gloved hand by a glove-puncturing object is surprisingly common, particularily to health care workers. The glove puncturing object may be either blunt or sharp edged. Frequently cited objects causing accidental glove puncture have included hypodermic syringe needles, suture needles, scapel blades, mechanical devices, medical instruments, blunt forceps, hemostats, glass slides and accessory medical objects such drill tips, chisels, saws, wires and glass objects. The edge of the glove-puncturing object depicted in FIG. 2A, FIG. 2B, FIG. 2C, and in FIG. 2D is sharp. A sharp object is depicted here only for illustrative purposes and is not meant to be a limiting example. The glove puncturing object could well be a blunt-edged object. The interactions illustrated in the Figures between the glove-puncturing object 6, glove layer 2, glove layer 3, the liquid antiseptic composition 4 and hand 8 would be approximately the same for any glove-puncturing object, as will become readily apparent from the following detailed description of these interactions.

FIG. 2A illustrates a cross-section of a glove wall along Line 5—5 as shown in FIG. 1A. A glove-puncturing object 6 is puncturing a glove on a hand 8 at a glove wall puncture 10. Object 6 may be contaminated with blood, other body fluids, other solids and mixtures therof. In addition, object 6 may be contaminated with an infectious pathogen. The contamination of the glove-puncturing object 6 is not been depicted in these Figures. The three arrows in FIG. 2A indicate the direction of motion for object 6. The contact angle of object 6 with the glove wall is not critical for function of the present invention.

It is another object of the present invention to provide a coating 7 of liquid antiseptic composition onto the puncturing portion of object 6. When object 6 punctures an outer glove layer 2 and contacts a compartment 4 storing the liquid antiseptic composition, object 6 can obtain a coating 7 of liquid antiseptic composition.

It is another object of the present invention to transfer a portion of coating 7 from object 6 to the space between inner glove layer 3 and hand 8. In FIG. 2B, object 6 has completely punctured the glove wall by puncturing inner glove layer 3. Coating 7 of liquid antiseptic composition on object 6 may then flow off object 6 into the space between inner glove layer 3 and hand 8.

It is another object of the present invention to transfer a portion of coating 7 to a hand wound 9, should the wound occur: wounding can be caused in the process of the continued motion of object 6 into the surface of hand 8. Depending upon the depth of penetration of object 6 into the hand, the hand wound 9 may be shallow or deep. Prior to contacting the gloved hand, object 6 may have been contaminated; the contaminant may include an infectious pathogen, blood, other body fluids, other solids and mixtures thereof. The infectious pathogens transferred from object 6 to hand 8 or hand wound 9 may cause a hand infection and/or a systemic infection. As discussed, the risk of an infection in the gloved individual may be lowered significantly by immediately treating the hand and the hand wound with a liquid antiseptic composition. A contamination of hand 8 or hand wound 9 by object 6 can be particularily hazardous for example if object 6 was contaminated with HIV or Hepatitis B virus. Thus, one method by which a glove in accordance with present invention functions is by using the glove puncturing object as a means for transferring some liquid antiseptic composition to the hand and to hand wound at the same time that the object may be transferring an innoculum of an infectious pathogen to the hand and into the hand wound caused by the glove-puncturing object. This function of the present invention can help to provide an immediate treatment of liquid antiseptic composition to the hand and to the hand wound and thereby help to prevent the establishment of a pathogenic systemic infection in the gloved individual as a result of the glove puncture.

It is another object of the present invention as illustrated in FIG. 2C, to have glove wall puncture 10 function to leak liquid antiseptic composition from compartment 4 after object 6 has been removed from the glove wall. Some leakage of liquid antiseptic composition from the compartment may take place before the glove puncturing object is actually removed from the glove. However, liquid antiseptic composition can flow more rapidly through inner glove layer 3 using the hole left by puncture 10 and can flow then onto hand 8 and into hand wound 9. This leak of liquid antiseptic composition can be used to further treat hand 8 and hand wound 9 to help to prevent the development of a pathogenic systemic infection therein.

It is another object of the present invention as illustrated in FIG. 2C, to enable the glove wearer or any other individual observing the gloved hand to more quickly see puncture site 10 and where the leak of liquid antiseptic composition arises out through outer glove layer 2 when the glove is damaged. To accomplish this objective, the liquid antiseptic composition may contain a color&hr. The colorant may consist of one or more dyes and/or one or more opacifiers or any combination therein. Some nonlimiting examples of the colorants that could be used in the liquid antiseptic composition include one or more of the following dyes: FD&C Yellow No.5, FD&C Yellow No.6, D&C Yellow No.10, FD&C Red No.3, FD&C Red No.40, D&C Red No.28, D&C Red No.30, D&C Red No. 33, FD&C Blue No.1, FD&C Blue No.2., FD&C Green No.3, D&C Green No.5, yellow iron oxide, black iron oxide, red iron oxide, brown iron oxide, and mixtures thereof or another acceptable dye. The colorant may be combined with one or more of the following opacifiers: white titanium dioxide, white calcium carbonate, white zinc sulfate, white zinc oxide, yellow iron oxide, black iron oxide, red iron oxide, brown iron oxide, and mixtures thereof or another acceptable opacifier. The location of the glove leak may also be used to help to quickly determine where and if the hand underneath the glove has been wounded.

Another object of the present invention is to have a smaller hole in outer glove layer 2 than in inner glove layer 3, after the glove-puncturing object has been removed from glove wall at puncture 10. This particular objective of the present invention has been depicted in FIG. 2C. The relative difference in the size of the puncture holes in the glove layers may be optimized in part by selecting a material composition for inner glove layer 3 that is less elastic and more plastic (and thus more capable of bursting and irreversibly tearing when punctured) than the material composition selected for outer glove layer 2. Controlling the relative size of the holes in the outer and inner glove layers can help to bias the direction of the leakage of the liquid antiseptic composition from the glove so that most of the leakage through puncture 10 occurs across inner glove layer 3 onto hand 8 and into hand wound 9, rather than across outer glove layer 2.

It is another object of the present invention to provide a prophylactic treatment of liquid antiseptic composition to the hand and to the hand wound should the wound occur when a glove wall puncture 10 is caused by an object whether or not the object is known to be contaminated with an infectious pathogen. The treatment can be an immediate and effective method for helping to prevent an infection to the hand, the hand wound, and the systemic circulation of an individual. The liquid antiseptic composition transferred to the hand and the hand wound can flow over the hand and into the hand wound. The liquid nature of the liquid antiseptic composition is extremely useful; the liquid permits the antiseptic to mix initimately with the biological contamination and infectious pathogen that is present on glove-puncturing object 6 and transferred by the glove-puncturing object to hand 8 and into hand wound 9. The liquid antiseptic composition can help to begin to disinfect hand 8 and hand wound 9 immediately by inactivating, killing and/or otherwise destroying any infectious pathogen transferred to the hand and the hand wound.

In another embodiment of the present invention the glove can be designed so that the liquid antiseptic composition in compartment 4 may be redistributed to better meet the needs of the glove wearer following an accidental glove wall puncture. In other words, the glove wearer can massage the glove wall to force the liquid antiseptic composition in compartment 4 to accumulate near the glove wall having the hole (the hole in glove wall puncture 10). The thickness of compartment 4 in the glove wall is increased in FIG. 2D compared to FIG. 2C to illustrate the point that an accumulation of the liquid antiseptic composition may occur in compartment 4 near glove wall puncture 10 as a result of glove massage; the accumulation can cause the liquid antiseptic composition in compartment 4 to leak at an increased rate onto the hand and into the hand wound, and can provide additional liquid antiseptic composition to treat hand 8 and hand wound 9 and as a result can provide additional protection to hand 8 and to hand wound 9. When the risk of infectious pathogen contamination to hand 8 and hand wound 9 is perceived by the gloved individual, even reflex glove massage may be particularily effective method of using the glove to quickly mobilize liquid antiseptic composition to where it is best needed.

Should the leakage of liquid antiseptic composition from puncture site 10 of outer glove layer 2 be deemed too excessive, the outward leak can be attenuated or stopped as desired if the glove wearer blocks puncture site 10 in outer glove layer 2 with a finger, a piece of tape, or some another material such as a piece of paper towel. Controlling outward leakage from the glove may help to insure that a sufficient leakage of liquid antiseptic compositon through puncture site 10 of inner glove layer 3 can occur onto hand 8 and into hand wound 9.

To make a glove in accordance with the present invention which has an outer glove layer and an inner glove layer of similar elasticity and similar plasticity, similar materials forming these glove layers may be used and may comprise: (a) a structural material selected from the group consisting of latex rubber, cis-1,4-polyisoprene, cis-polybutadiene, neoprene rubber, nitrile rubber, silicone rubber, another suitable rubber, cellulose acetate plastic, vinyl plastic, polyethylene plastic, polypropylene plastic, polyvinyl chloride plastic, polyvinyl acetate plastic, polystyrene plastic, polymethyl methyl-acrylate plastic, polyacrylonitrile plastic, vinyllite plastic, saran plastic, polytetrafluoroethylene plastic, polytrifluorochloroethylene plastic, polycaprolactam plastic, polyester plastic, urea formaldehyde plastic, polyurethane plastic, isotactic polypropylene plastic, nylon plastic, rayon plastic, polyamide plastic, phenolic plastic, silicone plastic, another suitable plastic, silk fiber, suitable fiber from an animal secretion, cotton fiber, cellulose fiber, another suitable plant fiber, wool fiber, another suitable animal fiber, animal hair, animal skin, animal intestinal tissue, animal connective tissue, another suitable animal tissue, metal fiber, mineral fiber, another suitable synthetic fiber, and mixtures thereof; and (b) a colorant selected from the group consisting of titanium oxide, an iron oxide, a dye and mixtures thereof. In general, materials that form liquid permeable layers may be coated or embedded with a liquid-impermeable material to render the glove layer liquid-impermeable.

Alternatively, to make a glove in accordance with the present invention having an inner glove layer of lower elasticity and higher plasticity than the outer glove layer, the first material (which is used for the outer glove layer) may comprise an elastic structural material selected from the group consisting of latex rubber, cis-1,4-polyisoprene rubber, cis-polybutadiene rubber, neoprene rubber, nitrile rubber, silicone rubber, another suitable rubber and mixtures thereof; and a colorant selected from the group consisting of titanium oxide, an iron oxide, a dye and mixtures thereof. The second material (used for the inner glove layer) may comprise: a plastic structural material selected from the group consisting of cellulose acetate plastic, vinyl plastic, polyethylene plastic, polypropylene plastic, polyvinyl chloride plastic, polyvinyl acetate plastic, polystyrene plastic, polymethyl methylacrylate plastic, polyacrylonitrile plastic, vinyllite plastic, saran plastic, polytetrafluoroethylene plastic, polycaprolactam plastic, polytrifluorochloroethylene plastic, nylon plastic, rayon plastic, polyester plastic, urea formaldehyde plastic, polyurethane plastic, isotactic polypropylene plastic, polyamide plastic, phenolic plastic, silicone plastic, another suitable plastic, silk fiber, another suitable fiber from an animal secretion, cotton fiber, another suitable plant fiber, wool fiber, another suitable animal fiber, animal hair, animal skin, animal intestinal and connective tissues, metallic fiber, mineral fiber, chemically-modified natural fibers, chemical-modified synthetic fibers another synthetic fiber, and mixtures thereof; and a colorant selected from the group consisting of titanium oxide, an iron oxide, a dye and mixtures thereof. Materials obtained from animal intestinal tissues and animal connective tissue may comprise the intestinal wall, ligaments, tendons and fascia and like tissue obtained from slaughtered farm or ranch animals including the following animals: cow, bull, sheep, steer, horse, chicken, goat, mink, rabbit, and pig. Any animal may provide suitable raw materials for the glove.

The colorants may be homogeneously mixed with the glove wall structural materials to color the materials and/or to opacify the materials. Alternatively one or more colorants or opacifiers and mixtures thereof may be printed onto the glove wall or may color the wall with a design or pattern that renders the glove wall opaque or colored in a more pleasing decoration. The design or pattern may have an appealing look or look funny so that the patient of the glove wearer is less anxious and less frightened, and is amused or calmed by the glove wearer; this effect is particularily useful for calming children and other patients of a gloved medical doctor or other health care worker. The design on the gloves may in addition have a positive impact on the glove wearer or provide written instructions or reminders to a gloved worker of a procedure for example. Glove coloration or opacity can also be used to help to make a glove in accordance with the present invention have the appearance of a conventional medical glove. The coloration or opacity of the glove wall can be used to obscure the presence of the liquid antiseptic composition contained within the thin glove wall of the present invvention.

A glove in accordance with the present invention will contain a liquid antiseptic composition which comprises one or more antiseptics in at least one liquid. As previously mentioned, a liquid may function for some embodiments of the present invention as both the antiseptic and the liquid in the liquid antiseptic composition. An example is a liquid antiseptic composition that is pure ethanol, pure isopropanol, or another liquid with an antiseptic property. The antiseptic used in some embodiments of the present invention may be selected from the group consisting of chlorhexidine gluconate, chlorhexidine acetate, other chlorhexidine salts, octoxynol, nonoxynol-9, methanol, ethanol, isopropanol, allyl alcohol, sodium hypochlorite, potassium hypochlorite, sodium dichloroisocyanurate, hypochlorous acid, acetic acid, sodium acetate, trichloroacetic acid, benzoic acid, sodium benzoate, boric acid, sodium borate, lactic acid, sodium lactate, chloramine, elemental iodine, sodium iodide, potassium iodide, calcium iodide, ammonium iodide, ferrous iodide, strontium iodide, lithium iodide, magnesium iodide, zinc iodide, silver iodide, selenium iodide, other iodide salts, povidone-iodine, iodinated organic compounds, bromide salts, brominated organic compounds, suitable flouride salts, formaldehyde, glutaraldehyde, mercurous chloride, zinc nitrate, zinc sulfate, zinc oxide, zinc acetate, zinc chloride, silver nitrate, silver sulfadiazine, hydrogen peroxide, benzoyl peroxide, phenol, sodium phenolate, cresol, methylphenol, resorcinol, orthophenylphenol, chloroxylenol, hexyl-resorcinol, parachlorophenol, paratertiary-amylphenol, thymol, butylparaban, ethylparaben, methylparaben, propylparaben, triclosan, o-benzyl-p-chlorophenol, hexachlorophene, poloxamer 188, benzalkonium chloride, benzethonium chloride, cetylpridinium chloride, econazole, methylbenzethonium chloride, cetyldimethylbenzylammonium chloride, triclocarban, clotrimazole, ciclopirox olamine, undecylenic acid, miconazole, tolnaftate and mixtures thereof.

The liquid antiseptic composition can be selected to be capable of specifically killing, inactivating and/or otherwise destroying a particular infectious pathogen. Alternatively, the liquid antiseptic composition may be designed to have a broad spectrum antiseptic activity against infectious pathogens. A glove in accordance with the present invention may contain formulations of the liquid antiseptic composition having potent antiseptic activity against HIV or Hepatitis B virus.

Preferably the antiseptic used in the glove is selected from the group consisting of povidone-iodine, elemental iodine, sodium iodide, potassium iodide, sodium hypochlorite, nonoxynol-9, and chlorhexidine gluconate and mixtures thereof because these antiseptics can have effective viricidal or antiviral activity.

The inclusion of a metal ion chelator such as EDTA, EGTA, NTA, HEDTA or other ion chelator at a concentration of between about 5 micromolar to about 5000 micromolar, in the liquid antiseptic composition may be useful to help preserve the activity of the antiseptic by chelating ions (cartons or anions) which may chemically inactivate the antiseptic. Other preservatives which may be added to the liquid antiseptic composition include pH buffers of ascorbic acid and ascorbate salts, phosphate pH buffers, other pH buffers, free radical scavengers, and reducing agents such as dithiothreitol (DTT). Antiseptics whose activity may be stabilized by a metal ion chelator or pH buffer include at least the following antiseptics: hydrogen peroxide, benzoyl peroxide, other peroxide antiseptics, sodium hypochlorite, potassium hypochlorite, sodium dichloroisocyanurate, hypochlorous acid, iodine, sodium iodide, potassium iodide and other halogen-releasing antiseptics.

The liquid antiseptic composition may contain a liquid selected from the group consisting of water, methanol, ethanol, isopropanol, propanol, allyl alcohol, butanol, isobutanol, sec-butanol, tertbutanol, benzyl alcohol, 2-octyl dodecanol, other liquid alcohols, glycerol, propylene glycol, a polyethylene glycol of about 150 to about 600 molecular weight, other liquid polyethylene glycols, other liquid glycols, urea, other liquid amides, acetone, methyl ethyl ketone, ethyl ketone, methyl isopropyl ketone, 2-pentanone, ethyl acetate, ethyl propionate, ethyl butyrate, ethyl valerate, methyl acetate, propyl acetate, butyl acetate, pentyl acetate, isopentyl acetate, benzyl acetate, other liquid ketones, other liquid esters, other liquid aldehydes, mineral oil, silicone oil, other synthetic oils, hexamethyl disiloxane, other liquid silanes, glycerol trioctanoate, decyl oleate, cetearyl isononanoate, other liquid soaps, other liquid detergents, dimethicone, other liquid silicones, perfluropolymethylisopropyl ether of about 1500 to about 6600 molecular weight, other liquid emulsifiers, olive oil, cottonseed oil, corn oil, soybean oil, wheat germ oil, linseed oil, pine oil, almond oil, macadamia oil, coconut oil, jojoba oil, peanut oil, persia oil, castor oil, other vegetable oils, other plant oils, cod liver oil, shark liver oil, mink oil, other animal oils, squalene, other liquid steroids, other suitable naturally occurring liquids, other suitable man-made liquids, and mixtures thereof.

Suitable materials, suitable liquids and other suitable chemicals which may be used in the present invention are considered "suitable" for the present invention when these substances (1) function as required by the invention at the concentration used, and (2) at that concentration cause only acceptably adverse side-effects and toxicity to the human body. For example, some of the more powerful liquid antiseptic compositions in the present invention will protect a gloved individual from acquiring a systemic HIV infection from an HIV and blood-tainted needlestick injury to a hand, but in the process will probably at least temporarily impair the healing process of the needlestick wound. Such a negative effect of the present invention should be weighed against the fact that the present invention can also prolong human life and productivity.

It is generally useful to add to the liquid antiseptic composition, at least one surface active agent to facilitate the coating of the glove-puncturing object with the liquid antiseptic composition. The surface active agent may be selected from the group consisting of dodecyldimethylamine oxide, lauryldimethylamine oxide, stearic acid, dibutyl adipate, octyl stearate, sodium cetearyl stearate, isopropyl myristrate, palmitic acid, stearyl alcohol, colloidal magnesium aluminum silicate, caprylic triglyceride, capric triglyceride, decyl-beta-D-glucopyranoside, cetostearyl alcohol, nonyl-beta-D-glucopyranoside, octyl-beta-D-glucopyranoside, triethanolamine stearate, sodium lauryl sulfate, heptyl-beta-D-glucopyranoside, hexyl-beta-D-glucopyranoside, dodecyl-beta-D-maltoside, decyl-beta-D-maltoside, sodium dodecylsulfate, sodium oleate, potassium laurate, sodium laurate, sodium lauryl sulfate, glycerol monostearate, propylene glycol monostearate, bis(2-ethylhexyl)sodium sulfosuccinate, N-octylsulfobetaine, propylene glycol monolaurate, N-dodecylsulfatobetaine, octyl-beta-D-thioglucopyranoside, heptyl-beta-D-thioglucopyranoside, N-dodecyl-N,N-dimethyl-glycine, cetyl alcohol, N-decylsulfatobetaine, digitonin, N-hexyadecylsulfatobetaine, N-tetradecylsulfatobetaine, dioctyl sodium sulfosuccinate, N,N,bis(3-D-gluconamidopropyl)cholamide, sodium deoxycholate, N,N,bis(3-D-gluconamidopropyl)deoxycholamide, glycerol monostearate, sodium taurodeoxycholate, sodium cholate, sodium taurocholate, sodium glycocholate, cetyltrimethylammonium bromide, 3-[(3-cholamidopropyl)dimethylammonio]-1-propanesulfonate, 3-[(3-cholamidopropyl)dimethylammonio]-2-hydroxypropane-1-sulfonate, octanoyl-N-methylglucamide, nonanoyl-N-methylglucamide, decanoyl-N-methylglucamide, nonyl-N-methylglucamide, lecithin, lysolecithin, nonaethylene glycol monododecyl ether, nonaethylene glycol octylphenol ether, nonaethylene glycol octylcyclohexyl ether, heptaethylene glycol octylphenyl ether, heptaethylene glycol octylcyclohexyl ether, polyoxyethylene (10) monolauryl ether, polyoxyethylene (8) isotridecyl ether, polyoxyethylene (10) isotridecyl ether, polyoxyethylene (15) isotridecyl ether, polyoxyethylene (9) lauryl ether, polyoxyethylene (23) lauryl ether, octaethylene glycol monododecyl ether, nonaethylene glycol monododecyl ether, polyethylene polypropylene glycol, sorbitan monopalmitate, sorbitan monooleate, sorbitan monostearate, polyoxyethylene sorbitan monolaurate, polyoxyethylene sorbitan monooleate, polyoxyethylene-4-lauryl ether, polyethylene glycol 400 monostearate, polyoxyethylene-4-sorbitan monolaurate, polyoxyethylene-20-sorbitan monooleate, polyoxyethylene-20-sorbitan monopalmitate, polyoxyethylene-20-sorbitan monolaurate, polyoxyethylene-40-stearate, dimethicone, simethicone, dimethylpolysiloxane, sorbitan trioleate, sorbitan tristreate, propylene glycol monostearate, sorbitan sesquioleate, diphenylmethylsilicone, lauryldimethylbenzylammonium chloride, a perfluropolymethylisopropyl ether of about 1500 to about 6600 molecular weight, acacia, type A gelatin, type B gelatin, egg yolk phospholipids, soybean phospohlipids, cholesterol, colloidal aluminum silicate, colloidal magnesium hydroxide, other suitable surface active agents, and mixtures thereof.

The liquid antiseptic composition may contain an algesic agent to increase the pain sensation perceived from a hand to alert the individual when the hand has been wounded by a glove-puncturing object. The algesic agent may be selected from the group consisting of formic acid, acetic acid, citric acid, sodium hydrogen citrate, other acidic citrate salts, other algesic organic acids, phosphoric acid, sodium hydrogen phosphate, sodium phosphate, potassium hydrogen phosphate, other acidic phosphate salts, other phosphate salts, hydrochloric acid, sulfuric acid, sodium hydrogen sulfate, sodium sulfate, other acidic sulfate salts, other algesic mineral acids, sodium hypochlorite, potassium hypochlorite, other hypochlorate salts, bradykinin, substance P, bee venom, wasp venom, ant venom, other suitable algesic animal algesics, other algesic peptides, algesic proteins, algesic ionophores, potassium chloride, potassium citrate, potassium sulfate, potassium phosphate, potassium carbonate, potassium bromide, potassium iodide, potassium fluoride, potassium hydroxide, potassium nitrate, other potassium salts, other potassium containing chemicals, other algesic organic chemicals, other algesic salts, and mixtures thereof.

The liquid antiseptic composition may also contain a colorant as a means for providing a colored visual signal to an individual when the glove wall has been punctured by the glove-puncturing object; the colorant is selected from the group consisting of the forementioned dyes, iron oxides, titanium dioxide and mixtures thereof. The colorant in the liquid antiseptiuc composition, glove walls, or on the glove wall surfaces may be fluorescent, phosphorescent, or glow in the dark after exposed to light as a means of enhancing the coloration.

Coloration may also be employed using one or more of the forementioned colorants to decorate the glove wall to give a glove in accordance with the present invention a more pleasant appearance. In some embodiments of the present invention, a colored design or pattern is envisioned which comprises a pattern of small animals including such as teddy bears, lions, giraffes, monkeys, dogs, cats, mice, cows, chickens, pigs, sheep, elephants, birds and the like animals. Other Figures decorating the glove may include clowns, toys, fire trucks, cowboys, outdoor scenes and the like; in general any scene or object which is pleasing to children and other individuals is imagined to be a useful decoration for the present invention. Glove coloration may be more abstract in pattern as well, may include a camouflage pattern, or more simply color the glove a single color such as pink, purple, white, green or any other color including a fluorescent color. Preferably glove wall coloration will render the glove wall opaque so that the liquid antiseptic composition within the glove wall is masked from being seen. In addition, printed diagrams, instructions, expressions, and any other information may be printed onto the glove wall and may accompany the coloration and glove wall decorations. Printing may appear alone on the glove wall. An important object of the glove wall coloration, decorations, and printing is to entertain and lessen the fears of the glove wearer, and/or the patients of the glove wearer. Such gloves should be particularily amusing to dental patients and other health care patients. The method of achieving the coloration, decoration and printing of the glove wall is not conceived to be limited to any paticular artistic or commercial art methodology.

The liquid antiseptic composition may further contain a concentration of vasocontricting agent ranging from about 1 part vasoconstricting agent in 200,000 parts of liquid antiseptic composition to about 1 part vasoconstricting agent in 2,000 parts of liquid antiseptic composition. Addition of a vasoconstricting agent to the liquid antiseptic composition is useful as a means for reducing blood flow in the hand wound to help to reduce the spreading of the infectious pathogen from the wound should the wound occur, into the systemic circulation (i.e., the blood circulation, lymphatic circulation, interstitial serum circulation, and other systemic fluid circulations) of an individual. The vasoconstricting agent may be selected from the well known group of vasocontricting ethylamine compounds or any other suitable group of vasoconstricting compounds. Preferably the vasoconstricting agent is selected from the group consisting of epinephrine, norepinephrine, phenylephrine, ephedrine, metaraminol, methoxamine and mixtures thereof.

The liquid antiseptic composition may further contain a viscosity-modifying chemical such as a polymer or a highly-branched molecule of high molecular weight, as a means for suitably adjusting the viscosity of the liquid antiseptic composition. The final viscosity of the liquid antiseptic composition may range from less than one centipoise to more than 5000 centipoise at normal glove temperatures which are generally expected to range between about 10° C. to about 45° C. Thus, the liquid antiseptic composition may have a low viscosity, similar to water, or may have a higher viscosity, for example the viscosity of a thick maple syrup or a bee honey. The viscosity-modifying polymer may be selected from the group consisting of xantham gum, gum acacia, gum tragacanth, agar, glycyrrhiza, sodium alginate, other plant gums, cellulose, methyl cellulose, carboxymethylcellulose sodium, other alkylated celluloses, other suitable chemically-modified celluloses, glycerol, propylene glycol, pyroxylin, polyethylene glycols of about 150 to about 600 molecular weight, other polyethylene glycols, gelatin, other proteins, dimethicone of about 100 to about 1000 centistokes viscosity, simethicone, dimethylpolysiloxane, perfluoropolymethylisopropyl ether of about 1500 to about 6600 molecular weight, starch, other alkylated starches, other chemically-modified starches, and mixtures thereof. Certain polymers such as starch or povidone or other molecules may complex iodine or other antiseptics and buffer their free concentration in the liquid antiseptic composition. This effect may need to be taken into account when formulating the liquid antiseptic composition.

The liquid antiseptic composition may also contain a chemical odor capable of causing either a pleasant or an unpleasant (malodorous) smell. The chemical smell may be caused an aromatic oil, a perfume, an ester, a ketone, an organic acid, a sulfide, an amine, a flower extract, a plant extract, an animal extract, a mineral extract, or another suitable chemical. When the glove is damaged, the chemical odor may be released from the compartment storing the liquid antiseptic composition; useful as a means for further alerting the glove wearer or others that a protective glove has been damaged.

Figure 3:
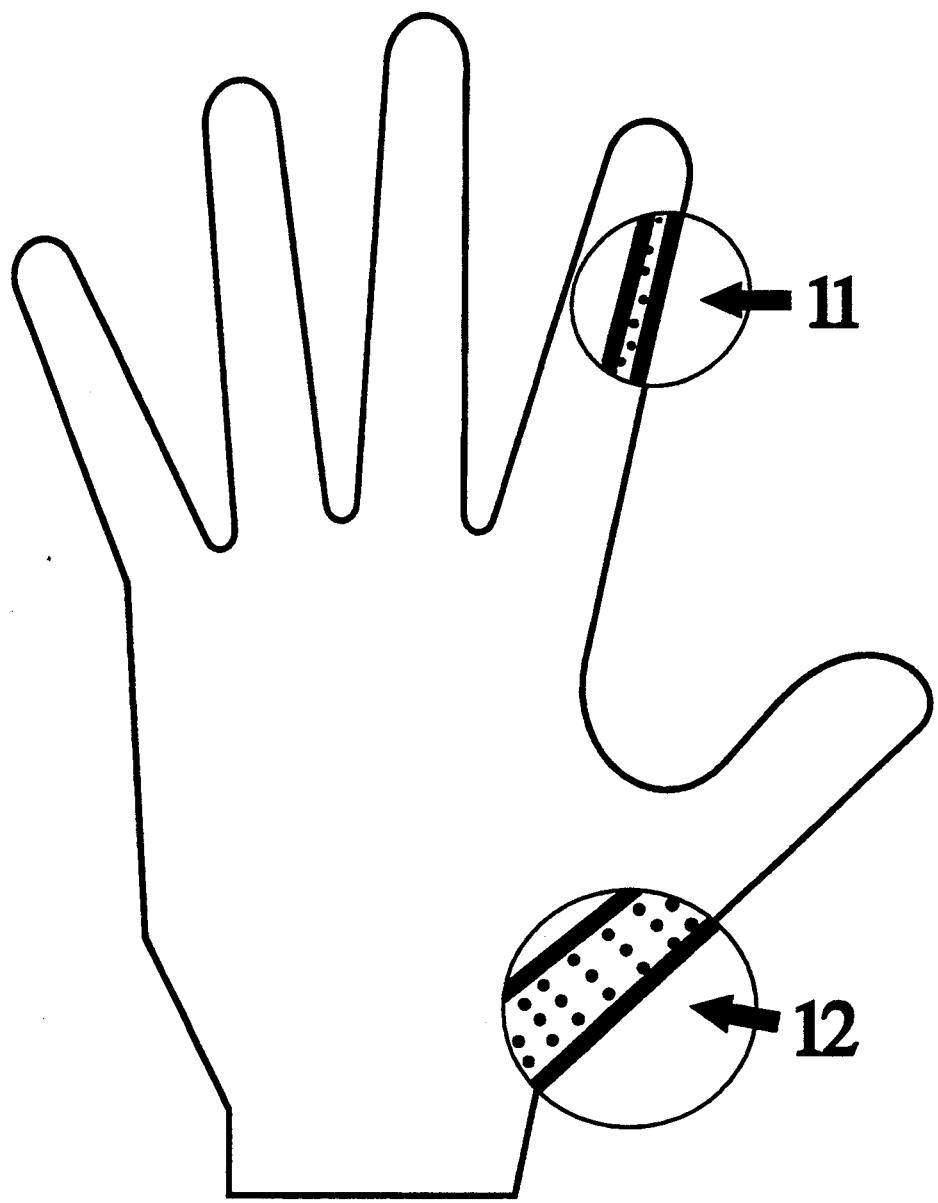
FIG. 3 illustrates a perspective view of a glove in accordance with the present invention, and a partial expanded view of a finger and a partial expanded view of the wrist area; the compartment storing liquid antiseptic composition is enlarged in the wrist area of the glove.

Another embodiment of the present invention can be seen by comparing the two partially enlarged sectional views of the glove encircled in FIG. 3: a finger wall sectional view 11 and a wrist wall sectional view 12. The thickness of compartment 4 storing liquid antiseptic composition in wrist wall 12 is significantly increased by design compared to the thickness of the compartment in finger wall 12. The entire wrist area of the glove is expanded by design so that the glove can store additional liquid antiseptic composition in the wrist area.

By massaging the glove in any manner, the stored liquid antiseptic composition can be redistributed by the glove wearer; useful as a means for forcing the liquid antiseptic composition to flow to other regions of the glove needing additional liquid antiseptic composition such as the site of glove damage as depicted in FIG. 2D where an accumulation of the liquid antiseptic composition can help to increase the leak of liquid antiseptic composition from the glove. A glove in accordance with the present invention may cover the fingers, palm, back of hand, wrist, forearm or arm; any of these regions of the glove can be modified by design so that a portion of compartment 4 in the selected region may store additional liquid antiseptic composition.

Once a particular formulation of liquid antiseptic composition has been chosen, a glove in accordance with the present invention can be made by many methods. One of the simplest ways to make a glove in accordance with the present invention is first to form the inner glove layer on a hand mold by one of the known methods used to form standard medical gloves. Any other suitable method that could make a glove layer is also acceptable. When the raw material to make the glove layer is available in a liquid form, the hand mold may be sprayed or dip coated with the liquid glove layer forming-material and allowed to solidify. The outer glove layer can then be formed on a second hand mold in the same manner. The outer glove layer can have larger dimensions so that a suitably-sized compartment 4 for the liquid antiseptic composition will be formed when the glove is assembled. After the glove wall layer materials have set, congealed, reacted, dried or solidified sufficiently, the outer surface of the inner glove layer may be suitably coated with, sprayed with, painted with or dip-coated with a selected amount of a liquid antiseptic composition. The outer glove layer can then be slipped over the liquid antiseptic coated inner glove layer. Extra liquid antiseptic composition can be drained from or added to the open end of compartment 4. The back ends of a glove in accordance with the present invention may be sealed to completely close compartment 4 or compartment 4 may be left open. A reversible seal may be used at the open wrist end of the glove which comprises a zip-locking connection between the glove layers or any other suitable connecting device. Alternatively, a glove in accordance with the present invention may have a simple structural design as has been described in FIG. 1A wherein inner glove layer 3 and outer glove layer 2 have no structural material connections. However, it may be disadvantageous to leave compartment 4 unsealed because the liquid antiseptic compostion may dry out or drain from the glove during glove storage or glove wear. In addition, when the liquid antiseptic composition is flammable, malodorous, or contains a colorant, then sealing compartment 4 may be more appropriate. Sealing of compartment 4 brings the inner and outer glove layers into physical contact so they become structurally connected at least at one point. A glue or any other means may be used to seal compartment 4 at the open end of the glove. A glue can be used which is capable of suitably bonding rubber, plastic and other glove layer materials forming the glove wall and which is not solubilized nor weakened by the liquid antiseptic composition. The preferred sealing glue may contain a silicone, an epoxy polymer, an epoxy resin, a cyanoacrylate, a cyanomethylacrylate, and the like, or any other glue or bonding agent that remains suitable in the presence of a particular liquid antiseptic composition.

Another alternative method of making a glove in accordance with the present invention is to first form each glove layer on a hand mold, and then slip (or slide) the outer glove layer over the inner glove layer. Some liquid antiseptic composition can then be added to suitably fill compartment 4 by using a tube, a funnel, by injection, by simple pouring of the liquid into compartment 4 or by any other method. The glove can then be sealed or left open at the glove end.

Another alternative method for making the present invention is to first add a liquid antiseptic composition to the inside of the chosen outer glove layer. Then the inner glove layer can be inserted within the outer glove layer. The glove can then be sealed or left open at the glove end.

As mentioned, the liquid antiseptic composition may simply be pure ethanol or another liquid having an antiseptic property. Thus, a glove in accordance with the present invention can be made rather easily by any individual using or wearing two gloves on each hand containing a liquid antiseptic composition between the gloves on each hand. The order of the steps by which the inner glove layer, outer glove layer, and the liquid antiseptic composition are combined to make the present invention is not in general critical.

Figure 4:
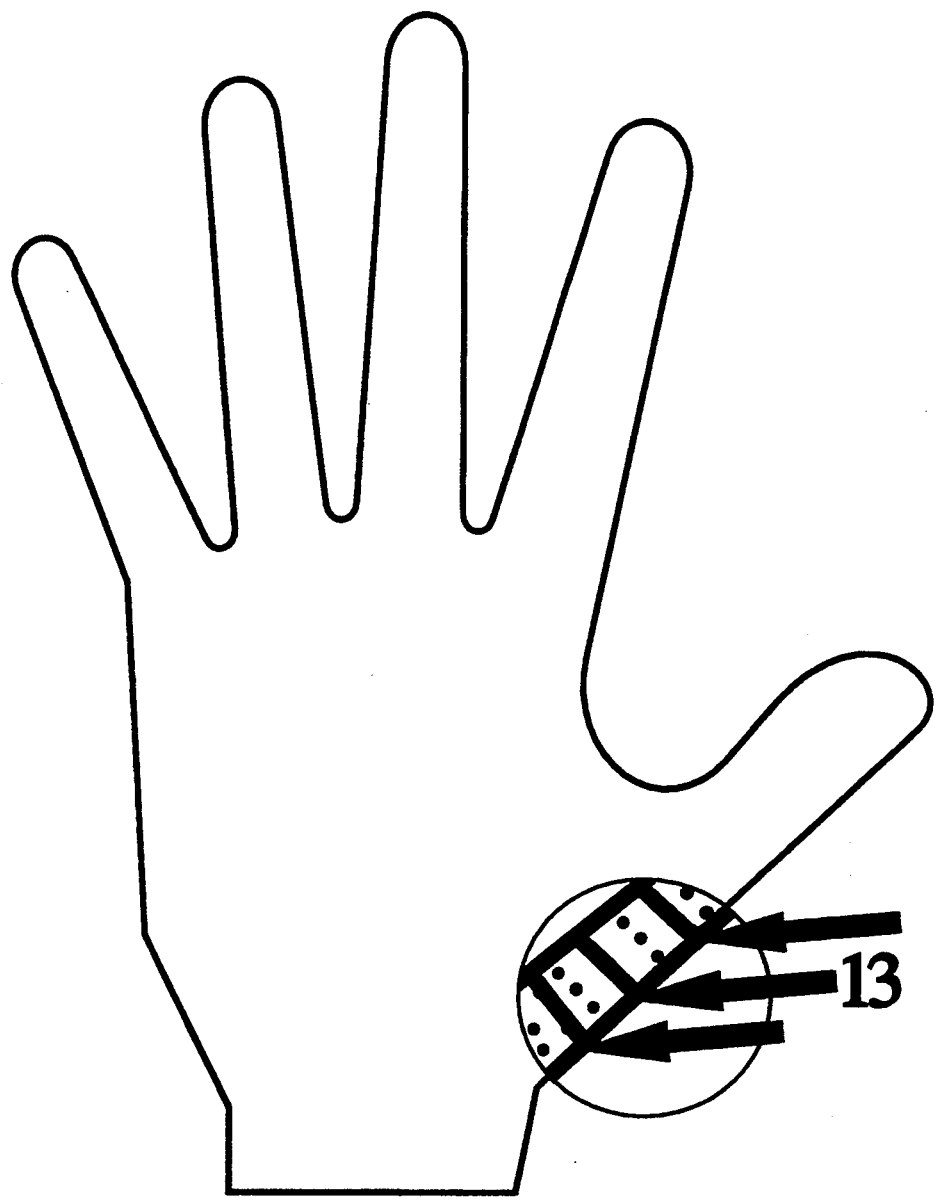
FIG. 4 illustrates a perspective view of a glove in accordance with the present invention with a partial expanded view of the glove wall; the glove has several structural connections between the innner layer and the outer layer of the glove.

Another embodiment of the present invention is illustrated in FIG. 4 in the encircled partially enlarged sectional view; the glove wall may have one structural connection, two structural connections, or a plurality of structural connection 13 (of a third material) in compartment 4 between the outer glove layer (first material) and the inner glove layer (second material). The third material forming a structural connection comprises:

(a) a structural material selected from the group consisting of latex rubber, cis-1,4-polyisoprene rubber, cis-polybutadiene rubber, neoprene rubber, nitrile rubber, silicone rubber, another rubber, cellulose acetate plastic, vinyl plastic, polyethylene plastic, polypropylene plastic, polyvinyl chloride plastic, polyvinyl acetate plastic, polystyrene plastic, polymethyl methylacrylate plastic, polyacrylonitrile plastic, vinyllite plastic, saran plastic, polytetrafluoroethylene plastic, polytrifluorochloroethylene plastic, nylon plastic, rayon plastic, polycaprolactam plastic, polyester plastic, urea formaldehyde plastic, polyurethane plastic, isotactic polypropylene plastic, polyamide plastic, phenolic plastic, silicone plastic, another plastic, another synthetic organic fiber, silk fiber, another suitable fiber from an animal secretion, cotton fiber, another plant fiber, wool fiber, another animal hair, leather, another animal fiber, animal skin, animal intestinal tissue, animal connective tissue, metallic fiber, mineral fiber, a glue comprising one or more of the forementioned structural materials, and mixtures thereof; and (b) a colorant selected from the group consisting of titanium dioxide, a dye, an iron oxide and mixtures thereof.

It is another object of the present invention to provide a glove having a plurality of glove layers acting as a structural connection which reconfigures the compartment storing the liquid antiseptic composition into a plurality of compartments capable of storing the liquid antiseptic composition.

It is another object of the present invention to provide a glove having a plurality of glove layers acting as a structural connection which reconfigures the compartment storing the liquid antiseptic composition into a plurality of compartments storing the components of the liquid antiseptic composition. For some embodiments of the present invention, it is conceivable that the chemical composition of the liquid antiseptic composition may be more stable, potent or otherwise more suitable when some of the components are kept physically separated from the rest until the glove wall is punctured. The glove wall puncture in this case would cause the components of the liquid antiseptic composition to mix together or to chemically react at the site of the wall puncture to form the liquid antiseptic composition to which the hand and hand wound would then be exposed as a treatment of liquid antiseptic composition.

It is another object of the present invention to provide a glove having a plurality of glove layers acting as a structural connection which reconfigures the compartment storing the liquid antiseptic composition into a plurality of compartments which macroscopically appear to the human eye (in a glove wall cross-section) to comprise a sponge. The spongy glove wall has a liquid impermeable coating or layer over at least the inner suface and outer surface of the glove wall to prevent leakage of the liquid antiseptic composition and to provide a suitable physical barrier. The liquid impermeable coating or layer may comprise one or more of the aformentioned structural glove wall materials. The size of each compartment storing the liquid antiseptic composition is not critical. Any of the compartments (for the present invention compartments may also be called subcompartments) may be microscopic in size, conceivably the pores in the spongy wall could be as small as five microns (five millionths of an inch) or have dimensions almost as large as the thickness of the glove wall.

It is another object of the present invention to provide a glove having a plurality of structural connections that can be used to strengthen the glove wall and/or which can be used to significantly reconfigure compartment 4 storing the liquid antiseptic composition into a plurality of subcompartments storing the liquid antiseptic composition. Every subcompartment or only a portion of the subcompartments may be connected to at least one adjacent subcompartment. Such a glove can be massaged to optimally redistribute the liquid antiseptic composition in the glove wall as illustrated in FIG. 2D.

Alternatively each subcompartment may be a closed space, in which case, glove massage would be marginally useful as a means for redistributing the liquid antiseptic composition within the glove wall. However, liquid antiseptic composition in the closed subcompartments could conceivably be stored at a positive pressure between normal atmospheric pressure and up to about three times atmospheric pressure, so that liquid antiseptic composition would be forcibly expelled from the pressurized subcompartments when an object punctured one or more of them. Glove massage might also help to expel the liquid antiseptic composition from this particular glove wall design.

Another embodiment of the present invention is to have a glove wherein only a portion of the subcompartments of the glove are closed and wherein a portion of the subcompartments are open so that the liquid antiseptic composition may flow from at least one subcompartment to another subcompartment.

According to another embodiment of the present invention, the compartment of the glove storing liquid antiseptic composition is connected to one or more additional reservoir(s) of liquid antiseptic composition by a one-way flow valve; a reservoir may be incorporated by design anywhere on the glove. Preferably an additional reservoir of liquid antiseptic composition would be located on the proximal (wrist) end of the glove. In some embodiments of the present invention, the additional reservoir retains only about 0.1 milliliters of liquid antiseptic composition. In other embodiments of the present invention, the additional reservoir retains up to about 25 milliliters of liquid antiseptic composition. The reservoir may be of a semi-spherical (dome) shape or an annular or a semi-annular design and may provide a manually-accessible reservoir of liquid antiseptic composition as needed for hand and hand wound irrigation. In the event of a hand wounding, the reservoir may be massaged, pushed, rolled forward, forcefully smacked down on a firm surface, or pressurized by any other means to release the liquid antiseptic composition from the reservoir to the compartment of the glove and from there to the hand wound site. Other conceivable means of resevoir massage are also acceptable. Any conceivable reservoir design may be acceptable, including a design incorporating a reinforced area within the glove which is capable of withstanding the pressure generated during reservoir massage. There may be a conduit with a one-way or "flapper" valve between the reservoir and compartment 4 of the glove. The one-way valve or flapper valve can be used to control the direction of liquid flow from the reservoir to the compartment of the glove so that liquid antiseptic composition does not flow back into the reservoir from the compartment of the glove; the object of the additional reservoir(s) is to provide an additional means for increasing the leakage of liquid antiseptic composition from compartment 4 of the glove when the glove wall has been punctured.

In another embodiment of the present invention a glove in accordance with the present invention contains a liquid antiseptic composition which comprises:
  (a) about 0.02 to about 20 parts of povidone-iodine;
  (b) about 0.1 to about 90 parts of water;
  (c) about 0.05 to about 30 parts of a polyoxyethylene glycol of about 150 to about 600 molecular weight; and
  (d) about 0.1 to about 90 parts of an alcohol, the alcohol selected from the group consisting of ethanol, isopropanol, propanol, n-butanol, sec-butanol, tert-butanol, benzyl alcohol, methanol, and mixtures thereof.

In another embodiment of the present invention a glove in accordance with the present invention contains a liquid antiseptic composition which comprises:
  (a) about 0.1 to about 20 parts of elemental iodine;
  (b) about 0.1 to about 20 parts of sodium iodide;
  (c) about 0.1 to about 30 parts of water;
  (d) about 0.05 to about 30 parts of a polyoxyethylene glycol of about 150 to about 600 molecular weight; and
  (e) about 0.1 to about 90 parts of an alcohol, the alcohol selected from the group consisting of ethanol, isopropanol, propanol, n-butanol, sec-butanol, tert-butanol, benzyl alcohol, methanol, and mixtures thereof.

In another embodiment of the present invention a glove in accordance with the present invention contains a liquid antiseptic composition which comprises:
  (a) about 0.1 to about 35 parts of sodium hypochlorite;
  (b) about 50 to 99 parts of water;

(c) about 0.05 to about 30 parts of a polyoxyethylene glycol of about 150 to about 600 molecular weight; and (d) about 0.1 to about 90 parts of an alcohol, the alcohol selected from the group consisting of ethanol, isopropanol, propanol, n-butanol, sec-butanol, tert-butanol, benzyl alcohol, methanol, and mixtures thereof.

In another embodiment of the present invention a glove in accordance with the present invention contains a liquid antiseptic composition which comprises:

(a) about 0.1 to about 25 parts of chlorhexidine gluconate;

(b) about 0.1 to about 90 parts of water;

(c) about 0.05 to about 30 parts of a polyoxyethylene glycol of about 150 to about 600 molecular weight; and (d) about 0.1 to about 90 parts of an alcohol, the alcohol selected from the group consisting of ethanol, isopropanol, propanol, n-butanol, sec-butanol, tert-butanol, benzyl alcohol, methanol, and mixtures thereof.

In another embodiment of the present invention a glove in accordance with the present invention contains a liquid antiseptic composition which comprises:

(a) about 0.1 to about 50 parts of nonoxynol-9;

(b) about 0.1 to about 95 parts of water;

(c) about 0.05 to about 30 parts of a polyoxyethylene glycol of about 150 to about 600 molecular weight; and (d) about 0.1 to about 90 parts of an alcohol, the alcohol selected from the group consisting of ethanol, isopropanol, propanol, n-butanol, sec-butanol, tert-butanol, benzyl alcohol, methanol, and mixtures thereof.

The preferred embodiment (See Example 4 below) of the present invention is a flexible protective glove which comprises: an inner layer 3 of polyethylene plastic which is about 1 mil in thickness: an outer layer 2 of colored latex rubber which is between about 4 mils in thickness; and a compartment 4 containing approximately 10 milliliters of a liquid antiseptic composition comprising: between about 2.5 parts of elemental iodine, about 2.5 parts of sodium iodide, about 70 parts of ethanol, about 10 parts of distilled water, 0.01 parts of FD&C red dye No.40 (#40) and about 5 parts of polyoxyethylene glycol of about 400 grams per mole molecular weight: wherein compartment 4 has a preferred thickness ranging between about 1 mil to about 250 mils and is closed to prevent evaporation. Note here that the term "parts" is a measure used in the present invention meaning parts by weight and not parts by volume.

The following Examples illustrate this invention.

EXAMPLE 1

About 95 milliliters of a liquid antiseptic composition is formulated at 23° C. (degrees Centigrade) by combining 10 grams of povidone-iodine, 10 grams of distilled water, 5 grams of polyoxyethylene glycol 400 molecular weight, and 70 grams of isopropanol and mixing for three hours in a glass 200 milliliter flask. An inner glove layer of 5 mil thick latex rubber (first material) is formed and cured until dry on a first hand mold. A slightly larger outer glove layer of 5 mil thick white latex rubber (first material) is formed and cured until dry on a second hand mold, and then is evenly filled with the about 10 milliliters of the liquid antiseptic composition. The outer glove layer is then slipped over the inner glove layer on the first hand mold. The end of compartment 4 of the glove is sealed using a silicone containing glue.

EXAMPLE 2

About 95 milliliters of a liquid antiseptic composition is formulated at 23° C. by combining 10 grams of povidone-iodine, 10 grams of distilled water, 5 grams of polyoxyethylene glycol 400 molecular weight, and 70 grams of denatured ethanol and mixing for three hours in a glass 200 milliter flask. An inner glove layer of 5 mil thick polyethylene plastic (second material) is formed and cured until dry on a first hand mold. A slightly larger outer glove layer of 5 mil thick white latex rubber (first material) is formed and cured until dry on a second hand mold, and then is evenly filled with the about 10 milliliters of the liquid antiseptic composition. The outer glove layer is then slipped over the inner glove layer on the first hand mold. The end of compartment 4 of the glove is sealed using a silicone containing glue.

In a comparison test between glove materials made by the method of Example 1 and glove materials made by the method of Example 2, more liquid antiseptic composition was observed to leak from the inner layer of a glove made by the method of Example 2, than a glove made by the method of Example 1.

EXAMPLE 3

The gloves made for Example 3 are elongated in length compared to the other Examples of the present invention from a length of 12 inches to a length of 30 inches) to include a protective arm portion that could be extended to the shoulder and arm pit. About 285 milliliters of a liquid antiseptic composition is formulated at 23 C by combining 12 grams of elemental iodine, 1.5 grams of distilled water, 15 grams of polyoxyethylene glycol 400 molecular weight, and 270 grams of ethanol and mixing for three hours in a glass 500 milliliter flask. An inner glove layer of 5 mil thick polyethylene plastic (second material) is formed and cured until dry on a long-armed first hand mold. A slightly larger outer glove layer of 8 mil thick white latex rubber (first material) is formed and cured until dry on a long-armed second hand mold, and then is evenly filled with the about 100 milliliters of the liquid antiseptic composition. The outer glove layer is then slipped over the inner glove layer on the first hand mold. The end of compartment 4 of the glove is sealed using a silicone containing glue.

EXAMPLE 4

About 95 milliliters of a liquid antiseptic composition is formulated at 23° C. by combining 2.5 grams of elemental iodine, 2.5 grams of sodium iodide, 10 grams of distilled water, 5 grams of polyoxyethylene glycol 400 molecular weight, 0.01 grams of FD&C red dye No. 40, and 70 grams of ethanol and mixing for three hours in a glass 200 milliliter flask. An inner glove layer of 1 mil thick polyethylene plastic (second material) is formed and cured until dry on a first hand mold. A slightly larger outer glove layer of 4 mil thick white latex rubber (first material) is formed and cured until dry on a second hand mold, and then is evenly filled with the about 9 milliliters of the liquid antiseptic composition. The outer glove layer is then slipped over the inner glove layer on the first hand mold. The end of compartment 4 of the glove is sealed using a silicone containing glue.

EXAMPLE 5

About 95 milliliters of a liquid antiseptic composition is formulated at 23° C. by combining 2.0 grams of elemental iodine, 3.0 grams of sodium iodide, 50 grams of distilled water, 5 grams of polyoxyethylene glycol 400 molecular weight, 0.01 grams of FD&C red dye No. 40, and 35 grams of ethanol and mixing for three hours in a glass 200 milliliter flask. An inner glove layer of 4 mil thick polyethylene plastic (second material) is formed and cured until dry on a first hand mold. A slightly larger outer glove layer of 4 mil thick white latex rubber (first material) is formed and cured until dry on a second hand mold, and then is evenly filled with the about 10 milliliters of the liquid antiseptic composition. The outer glove layer is then slipped over the inner glove layer on the first hand mold. The end of compartment 4 of the glove is sealed using a silicone containing glue.

EXAMPLE 6

About 95 milliliters of a liquid antiseptic composition is formulated at 23° C. by combining 4.0 grams of sodium hypochlorite, 70 grams of distilled water, 5 grams of polyoxyethylene glycol 400 molecular weight, 0.01 grams of FD&C red dye No. 40, 0.5 grams of titanium dioxide, and 25 grams of ethanol and mixing for three hours in a glass 200 milliliter flask. An inner glove layer of 4 mil thick polyethylene plastic (second material) is formed and cured until dry on a first hand mold. A slightly larger outer glove layer of 5 mil thick white latex rubber (first material) is formed and cured until dry on a second hand mold, and then is evenly filled with the about 10 milliliters of the liquid antiseptic composition. The outer glove layer is then slipped over the inner glove layer on the first hand mold. The end of compartment 4 of the glove is sealed using a silicone containing rubber glue.

EXAMPLE 7

About 95 milliliters of a liquid antiseptic composition is formulated at 23° C. by combining 4.0 grams of sodium hypochlorite, 50 grams of distilled water, 5 grams of polyoxyethylene glycol 400 molecular weight, 0.5 grams of red iron oxide, 0.5 grams of titanium dioxide, and 45 grams of ethanol and mixing for three hours in a glass 200 milliliter flask. An inner glove layer of 3 mil thick polyethylene plastic (second material) is formed and cured until dry on a first hand mold. A slightly larger outer glove layer of 6 mil thick white latex rubber (first material) is formed and cured until dry on a second hand mold, and then is evenly filled with the about 10 milliliters of the liquid antiseptic composition. The outer glove layer is then slipped over the inner glove layer on the first hand mold. The end of compartment 4 of the glove is sealed using a silicone containing rubber glue.

EXAMPLE 8

About 95 milliliters of a liquid antiseptic composition is formulated at 23° C. by combining 5.0 grams of potassium hypochlorite, 40 grams of distilled water, 5 grams of polyoxyethylene glycol 400 molecular weight, 0.01 grams of FD&C red dye No. 40, and 50 grams of ethanol and mixing for three hours in a glass 200 milliliter flask. An inner glove layer of 6 mil thick polyethylene plastic (second material) is formed and cured until dry on a first hand mold. A slightly larger outer glove layer of 6 mil thick white latex rubber (first material) is formed and cured until dry on a second hand mold, and then is evenly filled with the about 10 milliliters of the liquid antiseptic composition. The outer glove layer is then slipped over the inner glove layer on the first hand mold. The end of compartment 4 of the glove is sealed using a silicone containing glue.

EXAMPLE 9

About 95 milliliters of a liquid antiseptic composition is formulated at 23° C. by combining 1.0 gram of sodium hypochlorite, 20 grams of distilled water, 5 grams of polyoxyethylene glycol 400 molecular weight, 0.01 grams of FD&C red dye No. 40, and 20 grams of isopropanol, 20 grams of ethanol, 10 grams of benzyl alcohol, 10 grams of propanol, 10 grams of tert-butanol and mixing for three hours in a glass 200 milliliter flask. An inner glove layer of 6 mil thick polyethylene plastic (second material) is formed and cured until dry on a first hand mold. A slightly larger outer glove layer of 6 mil thick white latex rubber (first material) is formed and cured until dry on a second hand mold, and then is evenly filled with the about 10 milliliters of the liquid antiseptic composition. The outer glove layer is then slipped over the inner glove layer on the first hand mold. The end of compartment 4 of the glove is sealed using a silicone containing glue.

EXAMPLE 10

About 95 milliliters of a liquid antiseptic composition is formulated at 23° C. by combining 4.0 grams of chlorhexidine gluconate, 50 grams of distilled water, 5 grams of polyoxyethylene glycol 400 molecular weight, 0.01 grams of FD&C red dye No. 40, and 20 grams of isopropanol, 20 grams of ethanol, and mixing for three hours in a glass 200 milliliter flask. An inner glove layer of 6 mil thick polyethylene plastic (second material) is formed and cured until dry on a first hand mold. A slightly larger outer glove layer of 6 mil thick white latex rubber (first material) is formed and cured until dry on a second hand mold, and then is evenly filled with the about 10 milliliters of the liquid antiseptic composition. The outer glove layer is then slipped over the inner glove layer on the first hand mold. The end of compartment 4 of the glove is sealed using a silicone containing glue.

EXAMPLE 11

About 95 milliliters of a liquid antiseptic composition is formulated at 23° C. by combining 4.0 grams of chlorhexidine gluconate, 50 grams of distilled water, 5 grams of polyoxyethylene glycol 400 molecular weight, 0.01 grams of FD&C red dye No. 40, and 20 grams of isopropanol, 20 grams of ethanol, and mixing for three hours in a glass 200 milliliter flask. An inner glove layer of about 0.3 mil thick polyethylene plastic (second material) is formed and cured until dry on a first hand mold. A slightly larger outer glove layer of about 3 mil thick white latex rubber (first material) is formed and cured until dry on a second hand mold, and then is evenly filled with the about 10 milliliters of the liquid antiseptic composition. The outer glove layer is then slipped over the inner glove layer on the first hand mold. The end of compartment 4 of the glove is sealed using a silicone containing glue.

EXAMPLE 12

About 95 milliliters of a liquid antiseptic composition is formulated at 23° C. by combining 2.5 grams of chlorhexidine gluconate, 50 grams of distilled water, 5 grams of polyoxyethylene glycol 400 molecular weight, 0.01 grams of FD&C red dye No. 40, and 40 grams of ethanol, and mixing for three hours in a glass 200 milliliter flask. An inner glove layer of 3 mil thick polyethylene plastic (second material) is formed and cured until dry on a first hand mold. A slightly larger outer glove layer of 3 mil thick white latex rubber (first material) is formed and cured until dry on a second hand mold, and then is evenly filled with the about 10 milliliters of the liquid antiseptic composition. The outer glove layer is then slipped over the inner glove layer on the first hand mold. The end of compartment 4 of the glove is sealed using a silicone containing glue.

EXAMPLE 13

About 95 milliliters of a liquid antiseptic composition is formulated at 23° C. by combining 2.5 grams of chlorhexidine gluconate, 50 grams of distilled water, 5 grams of polyoxyethylene glycol 400 molecular weight, 0.01 grams of FD&C red dye No. 40, and 40 grams of ethanol, and mixing for three hours in a glass 200 milliliter flask. An inner glove layer of 3 mil thick polyethylene plastic (second material) is formed and cured until dry on a first hand mold. A slightly larger outer glove layer of 3 mil thick white latex rubber (first material) is formed and cured until dry on a second hand mold, and then is evenly filled with the about 10 milliliters of the liquid antiseptic composition. The outer glove layer is then slipped over the inner glove layer on the first hand mold. The end of compartment 4 of the glove is sealed using a silicone containing glue.

EXAMPLE 14

About 95 milliliters of a liquid antiseptic composition is formulated at 23° C. by combining 1.2 grams of chlorhexidine gluconate, 15 grams of distilled water, 7 grams of polyoxyethylene glycol 400 molecular weight, 0.01 grams of FD&C red dye No. 40, and 75 grams of isopropanol, and mixing for three hours in a glass 200 milliliter flask. An inner glove layer of 5 mil thick polyethylene plastic (second material) is formed and cured until dry on a first hand mold. A slightly larger outer glove layer of 5 mil thick white latex rubber (first material) is formed and cured until dry on a second hand mold, and then is evenly filled with the about 10 milliliters of the liquid antiseptic composition. The outer glove layer is then slipped over the inner glove layer on the first hand mold. The end of compartment 4 of the glove is sealed using a silicone containing glue.

EXAMPLE 15

About 95 milliliters of a liquid antiseptic composition is formulated at 23° C. by combining 8.5 grams of nonoxynol-9, 75 grams of distilled water, 4 grams of polyoxyethylene glycol 400 molecular weight, 0.01 grams of FD&C red dye No. 40, and 8 grams of isopropanol, and mixing for three hours in a glass 200 milliliter flask. An inner glove layer of 5 mil thick polyethylene plastic (second material) is formed and cured until dry on a first hand mold. A slightly larger outer glove layer of 5 mil thick white latex rubber (first material) is formed and cured until dry on a second hand mold, and then is evenly filled with the about 10 milliliters of the liquid antiseptic composition. The outer glove layer is then slipped over the inner glove layer on the first hand mold. The end of compartment 4 of the glove is sealed using a silicone containing glue.

EXAMPLE 16

About 95 milliliters of a liquid antiseptic composition is formulated at 23° C. by combining 4.8 grams of nonoxynol-9, 35 grams of distilled water, 4 grams of polyoxyethylene glycol 400 molecular weight, 0.01 grams of FD&C red dye No. 40, and 45 grams of ethanol, and mixing for three hours in a glass 200 milliliter flask. An inner glove layer of 5 mil thick polyethylene plastic (second material) is formed and cured until dry on a first hand mold. A slightly larger outer glove layer of 6 mil thick white latex rubber (first material) is formed and cured until dry on a second hand mold, and then is evenly filled with the about 10 milliliters of the liquid antiseptic composition. The outer glove layer is then slipped over the inner glove layer on the first hand mold. The end of compartment 4 of the glove is sealed using a silicone containing glue.

EXAMPLE 17

About 95 milliliters of a liquid antiseptic composition is formulated at 23° C. by combining 4.8 grams of nonoxynol-9, 35 grams of distilled water, 5 grams of polyoxyethylene glycol 400 molecular weight, 0.005 grams of bradykinin, 0.005 grams of epinephrine, 0.01 grams of FD&C red dye No. 40, and 45 grams of ethanol, and mixing for three hours in a glass 200 milliliter flask. An inner glove layer of 5 mil thick polyethylene plastic (second material) is formed and cured until dry on a first hand mold. A slightly larger outer glove layer of 6 mil thick white latex rubber (first material) is formed and cured until dry on a second hand mold, and then is evenly filled with the about 10 milliliters of the liquid antiseptic composition. The outer glove layer is then slipped over the inner glove layer on the first hand mold. The end of compartment 4 of the glove is sealed using a silicone containing glue.

EXAMPLE 18

About 95 milliliters of a liquid antiseptic composition is formulated at 23° C. by combining 2.4 grams of nonoxynol-9, 35 grams of distilled water, 5 grams of polyoxyethylene glycol 400 molecular weight, 0.005 grams of bradykinin, 0.01 grams of FD&C red dye No. 40, and 45 grams of ethanol, and mixing for three hours in a glass 200 milliliter flask. An inner glove layer of 5 mil thick polyethylene plastic (second material) is formed and cured until dry on a first hand mold. A slightly larger outer glove layer of 6 mil thick white latex rubber (first material) is formed and cured until dry on a second hand mold, and then is evenly filled with the about 10 milliliters of the liquid antiseptic composition. The outer glove layer is then slipped over the inner glove layer on the first hand mold. The end of compartment 4 of the glove is sealed using a silicone containing glue.

EXAMPLE 19

About 95 milliliters of a liquid antiseptic composition is formulated at 23° C. by combining 7.5 grams of potassium iodide, 55 grams of distilled water, 5 grams of polyoxyethylene glycol 400 molecular weight, 0.01 grams of FD&C red dye No. 40, and 35 grams of ethanol, and mixing for three hours in a glass 200 milliliter flask. An inner glove layer of 6 mil thick polyethylene plastic (second material) is formed and cured until dry on a first hand mold. A slightly larger outer glove layer of 6 mil thick white latex rubber (first material) is formed and cured until dry on a second hand mold, and then is evenly filled with the about 10 milliliters of the liquid antiseptic composition. The outer glove layer is then slipped over the inner glove layer on the first hand mold. The end of compartment 4 of the glove is sealed using a silicone containing glue.

EXAMPLE 20

About 85 milliliters of a liquid antiseptic composition is formulated at 23° C. by combining 2.5 grams of elemental iodine, 3.5 grams of potassium iodide, 70 grams of ethanol, 10 grams of distilled water, 1 gram of polyoxyethylene glycol 400 molecular weight, and 0.01 grams of FD&C red dye No. 40, and mixing for three hours in a glass 200 milliliter flask. An inner glove layer of about 1 mil thick polyethylene plastic (second material) is formed and cured until dry on a first hand mold. A slightly larger outer glove layer of 4 mil thick white latex rubber (first material) is formed and cured until dry on a second hand mold, and then is evenly filled with the about 10 milliliters of the liquid antiseptic composition. The outer glove layer is then slipped over the inner glove layer on the first hand mold. The end of compartment 4 of the glove is sealed using a silicone containing glue.

EXAMPLE 21

About 85 milliliters of a liquid antiseptic composition is formulated at 23° C. by combining 2.5 grams of elemental iodine, 3.5 grams of potassium iodide, 70 grams of ethanol, 10 grams of distilled water, 1 gram of polyoxyethylene glycol 400 molecular weight, and 0.01 grams of FD&C red dye No. 40, and mixing for three hours in a glass 200 milliliter flask. An inner glove layer of about 30 mils thick polyethylene plastic (second material) is formed and cured until dry on a first hand mold. A slightly larger outer glove layer of 40 mils thick white latex rubber (first material) is formed and cured until dry on a second hand mold, and then is evenly filled with the about 14 milliliters of the liquid antiseptic composition. The outer glove layer is then slipped over the inner glove layer on the first hand mold. The end of compartment 4 of the glove is sealed using a silicone containing glue. The thicker glove layers of this embodiment of the present invention are designed to provide a strong physical barrier and still provide a glove with suitable flexiblity for some gloved workers.

While we have shown and described a number of embodiments of our invention, it will be apparent to those skilled in the art that many changes and modifications may be made without departing from our present invention in its broader aspects. We therefore intend the appended claims to cover all such changes and modifications as fall within the true spirit and scope of our present invention.

We claim:

1. A flexible protective glove with a liquid-impermeable wall having the capability to provide a liquid antiseptic composition treatment to a hand and to a hand wound should the wound occur underneath the glove while the glove is being worn when a wall of the glove is punctured by an object that may be contaminated with an infectious pathogen, comprising:

(a) a glove wall with a liquid-impermeable outer layer comprised of a first material having a thickness of about 1 mil to about 40 mils and a liquid-impermeable less elastic inner layer composed of a second material having a thickness of about 0.3 mils to about 30 mils wherein the first material and the second material form the walls of a compartment capable of containing a liquid antiseptic composition;

(b) the liquid antiseptic composition in the compartment which comprises an antiseptic in a liquid;

(c) the glove wall capable of providing a physical barrier as a means of protective to the hand while the glove is being worn by an individual until a portion of the glove wall is punctured by an object;

(d) the glove wall capable of being punctured by the object while the glove is being worn on the hand;

(e) the glove wall having the flexibility to allow the hand of an individual in need of wearing the glove to easily and adequately perform delicate, dexterous and complex work including the work performed by a surgeon, a medical doctor, a dentist, a laboratory worker, a health care worker, a law enforcement worker, a hospital worker, and other workers;

(f) the glove having the capability to provide a coating to at least a portion of the object puncturing the glove wall; the coating comprising the liquid antiseptic composition; the coating on the object providing a means for immediately transferring some of the liquid antiseptic composition onto the hand and into the hand wound by the object puncturing the glove wall while the glove is being worn; the liquid antiseptic composition transferred to the hand and to the hand wound having the capability to provide an immediate liquid antiseptic composition treatment to the hand and hand wound;

(g) the glove having the additional capability to leak some of the liquid antiseptic composition from a section of the glove wall having a hole resulting from the object puncturing the glove wall; the hole in the outer layer may shrink while the hole in the less elastic inner layer of the glove is not as capable of contracting to a small size; the liquid antiseptic composition leaking from the hole having the capability of flowing onto the hand and into the hand wound as a means for providing a treatment of liquid antiseptic composition to the hand and to the hand wound; more liquid antiseptic composition may leak from the glove wall onto the hand and into the hand wound than from the glove wall onto the outer surface of the glove; and (h) the glove having the capability of treating the hand and the hand wound with the liquid antiseptic composition when the object punctures the glove wall, when the object contacts the hand, when the object may wound the hand, and when the object may contaminate the hand and the hand wound with the infectious pathogen; wherein the liquid antiseptic composition transferred to the hand and the hand wound can help to protect the hand, the hand wound, and the systemic circulation of the individual by killing, inactivating, and otherwise destroying the infectious pathogen that may be contaminating the hand and the hand wound.

2. The glove according to claim 1, wherein the liquid antiseptic composition is capable of being redistributed within the compartment of the glove by massaging the glove to force the liquid antiseptic composition in the compartment to accumulate near the glove wall having the hole and to leak at an increased rate from the wall having the hole onto the hand and into the hand wound providing additional liquid antiseptic composition to treat the skin and the hand wound resulting in additional protection of the skin and hand wound from the infectious pathogen that may be contaminating the skin and the hand wound.

3. A glove according to claim 1, wherein the first material and the second material comprise:
(a) a structural material selected from the group consisting of latex rubber, cis-1,4-polyisoprene, cis-polybutadiene, neoprene rubber, nitrile rubber, silicone rubber, cellulose acetate plastic, vinyl plastic, polyethylene plastic, polypropylene plastic, polyvinyl chloride plastic, polyvinyl acetate plastic, polystyrene plastic, polymethyl methyl-acrylate plastic, polyacrylonitrile plastic, vinyllite plastic, saran plastic, polytetrafluoroethylene plastic, polytrifluorochloroethylene plastic, polycaprolactam plastic, polyester plastic, urea formaldehyde plastic, polyurethane plastic, isotactic polypropylene plastic, nylon plastic, rayon plastic, polyamide plastic, phenolic plastic, silicone plastic, silk fiber, cotton fiber, cellulose fiber, wool fiber, animal skin, animal intestinal tissue, animal connective tissue, metallic fiber, mineral fiber and mixtures thereof.

4. A glove according to claim 3, wherein the first material comprises: a structural material selected from the group consisting of latex rubber, cis-1,4-polyisoprene rubber, cis-polybutadiene rubber, neoprene rubber, and nitrile rubber, silicone rubber and mixtures thereof; and wherein the second material comprises: a structural material selected from the group consisting of cellulose acetate plastic, vinyl plastic, polyethylene plastic, polypropylene plastic, polyvinyl chloride plastic, polyvinyl acetate plastic, polystyrene plastic, polymethyl methylacrylate plastic, polyacrylonitrile plastic, vinyllite plastic, saran plastic, polytetrafluoroethylene plastic, polycaprolactam plastic, rayon plastic, polytrifluorochloroethylene plastic, nylon plastic, polyester plastic, urea formaldehyde plastic, polyurethane plastic, isotactic polypropylene plastic, polyamide plastic, phenolic plastic, silicon plastic, silk fiber, cotton fiber, plant fiber, wool fiber, animal skin, animal intestinal tissue, animal connective tissue, metallic fiber, mineral fiber, and mixtures thereof.

5. A glove according to claim 1, wherein the antiseptic is selected from the group consisting of chlorhexidine gluconate, chlorhexidine acetate, sodium dichloroisocyanurate, octoxynol, nonoxynol-9, ethanol, isopropanol, propanol, benzyl alcohol, allyl alcohol, methanol, sodium hypochlorite, potassium hypochlorite, hypochlorous acid, acetic acid, trichloroacetic acid, benzoic acid, sodium benzoate, boric acid, sodium borate, lactic acid, chloramine, elemental iodine, sodium iodide, potassium iodide, calcium iodide, ammonium iodide, ferrous iodide, strontium iodide, lithium iodide, magnesium iodide, zinc iodide, silver iodide, selenium iodide, povidone-iodine, formaldehyde, glutaraldehyde, mercurous chloride, zinc nitrate, zinc sulfate, zinc oxide, zinc acetate, zinc chloride, silver nitrate, silver sulfadiazine, hydrogen peroxide, benzoyl peroxide, phenol, sodium phenolate, cresol, methylphenol, resorcinol, orthophenylphenol, chloroxylenol, hexyl-resorcinol, parachlorophenol, para-tertiaryamylphenol, thymol, butylparaben, ethylparaben, methylparaben, propylparaben, triclosan, o-benzyl-p-chlorophenol, hexachlorophene, poloxamer 188, benzalkonium chloride, benzethonium chloride, cetylpridinium chloride, econazole, methylbenzethonium chloride, cetyldimethylbenzylammonium chloride, triclocarban, clotrimazole, ciclopirox olamine, undecylenic acid, miconazole, tolnaftate, and mixtures thereof.

6. A glove according to claim 1, wherein the liquid medium is selected from the group consisting of water, methanol, ethanol, isopropanol, propanol, allyl alcohol, butanol, isobutanol, sec-butanol, tert-butanol, benzyl alcohol, 2-octyl dodecanol, glycerol, propylene glycol, a polyethylene glycol of about 150 to about 600 molecular weight, urea, acetone, methyl ethyl ketone, ethyl ketone, methyl isopropyl ketone, 2-pentanone, ethyl acetate, ethyl propionate, ethyl butyrate, ethyl valerate, methyl acetate, propyl acetate, buryl acetate, pentyl acetate, isopentyl acetate, benzyl acetate, mineral oil, silicone oil, hexamethyl disiloxane, glycerol trioctanoate, decyl oleate, cetearyl isononanoate, dimethicone, perfluropolymethyisopropyl ether of about 1500 to about 6600 molecular weight, olive oil, cottonseed oil, corn oil, soybean oil, wheat germ oil, linseed oil, pine oil, almond oil, macadamia oil, coconut oil, jojoba oil, peanut oil, persia oil, castor oil, cod liver oil, shark liver oil, mink oil, squalene and mixtures thereof.

7. A glove according to claim 1, wherein the liquid antiseptic composition contains a surface-active agent to facilitate the coating of the object with the liquid antiseptic composition, the surface active agent selected from the group consisting of dodecyldimethylamine oxide, lauryldimethylamine oxide, stearic acid, dibutyl adipate, octyl stearate, sodium cetearyl stearate, isopropyl myristrate, palmitic acid, stearyl alcohol, colloidal magnesium aluminum silicate, caprylic triglyceride, capric triglyceride, cetostearyl alcohol, decyl-beta-D-glucopyranoside, nonyl-beta-D-glucopyranoside, octyl-beta-D-glucopyranoside, triethanolamine stearate, sodium lauryl sulfate, heptyl-beta-D-glucopyranoside, hexyl-beta-D-glucopyranoside, dodecyl-beta-D-maltoside, decyl-beta-D-maltoside, sodium dodecylsulfate, sodium oleate, potassium laurate, sodium laurate, sodium lauryl sulfate, glycerol monostearate, propylene glycol monostearate, bis(2-ethylhexyl)sodium sulfosuccinate, N-octylsulfobetaine, propylene glycol monolaurate, N-dodecylsulfatobetaine, octyl-beta-D-thioglucopyranoside, heptyl-beta-D-thioglucopyranoside, N-dodecyl-N,N-dimethylglycine, cetyl alcohol, N-decylsulfatobetaine, digitonin, N-hexyldecylsulfatobetaine, N-tetradecylsulfatobetaine, dioctyl sodium sulfosuccinate, N,N,bis(3-D-gluconamidopropyl)-cholamide, sodium deoxycholate, N,N,bis(3-D-gluconamidopropyl)-deoxycholamide, glycerol monostearate, sodium taurodeoxycholate, sodium cholate, sodium taurocholate, sodium glycocholate, cetyltrimethylammonium bromide, 3-[(3-cholamidopropyl)dimethylammonio]-1-propanesulfonate, 3-[(3-cholamidopropyl)dimethylammonio]-2-hydroxypropane-1-sulfonate, octanoyl-N-methylglucamide, nonanoyl-N-methylglucamide, decanoyl-N-methylglucamide, nonyl-N-methylglucamide, lecithin, lysolecithin, nonaethylene glycol monododecyl ether, nonaethylene glycol octylphenol ether, nonaethylene glycol octylcyclohexyl ether, heptaethylene glycol octylphenyl ether, heptaethylene glycol octylcyclohexyl ether, polyoxyethylene (10) monolauryl ether, polyoxyethylene (8) isotridecyl ether, polyoxyethylene (10) isotridecyl ether, polyoxyethylene (15) isotridecyl ether, polyoxyethylene (9)

lauryl ether, polyoxyethylene (23) lauryl ether, octaethylene glycol monododecyl ether, nonaethylene glycol monododecyl ether, polyethylene polypropylene glycol, sorbitan monopalmitate, sorbitan monooleate, sorbitan monostearate, polyoxyethylene sorbitan monolaurate, polyoxyethylene sorbitan monooleate, polyoxyethylene-4-lauryl ether, a polyethylene glycol of about 150 to about 600 molecular weight, polyethylene glycol 400 monostearate, polyoxyethylene-4-sorbitan monolaurate, polyoxyethylene-20-sorbitan monooleate, polyoxyethylene-20-sorbitan monopalmitate, polyoxyethylene-20-sorbitan monolaurate, polyoxyethylene-40-stearate, dimethicone, simethicone, dimethylpolysiloxane, sorbitan trioleate, sorbitan tristreate, propylene glycol monostearate, sorbitan sesquioleate, diphenylmethylsilicone, lauryldimethylbenzylammonium chloride, a perfluropolymethylisopropyl ether of about 1500 to about 6600 molecular weight, acacia, type A gelatin, type B gelatin, egg yolk phospholipids, soybean phospholipids, cholesterol, colloidal aluminum silicate, colloidal magnesium hydroxide, and mixtures thereof.

8. A glove according to claim 1, wherein the liquid antiseptic composition contains an algesic agent to increase the pain sensation perceived from the hand, to alert the individual when the hand has been wounded, the algesic agent selected from the group consisting of formic acid, acetic acid, hydrochloric acid, phosphoric acid, sodium hydrogen phosphate, sodium phosphate, potassium hydrogen phosphate, potassium phosphate, citric acid, sodium hydrogen citrate, sodium citrate, sulfuric acid, sodium hydrogen sulfate, sodium sulfate, sodium hypochlorite, potassium hypochlorite, bradykinin, substance P, bee venom, wasp venom, ant venom, potassium chloride, potassium citrate, potassium sulfate, potassium phosphate, potassium carbonate, potassium bromide, potassium iodide, potassium fluoride, potassium hydroxide, potassium nitrate, and mixtures thereof.

9. A glove according to claim 1, wherein the liquid antiseptic composition further contains a colorant as a means for providing a colored visual signal to the individual when and where the glove wall has been punctured by the object, the colorant selected from the group consisting of a dye, an iron oxide, titanium dioxide, and mixtures thereof.

10. A glove according to claim 1, wherein the liquid antiseptic composition further contains a vasoconstricting agent in a concentration of about 1 vasoconstricting agent part in 200,000 parts of the liquid antiseptic composition to about 1 vasoconstricting agent part in 2,000 parts of the liquid antiseptic composition as a means for reducing blood flow in the hand wound as a means for reducing a systemic spreading of the infectious pathogen in the individual, the vasoconstricting agent selected from the group consisting of epinephrine, norepinephrine, phenylephrine, ephedrine, metaraminol, methoxamine, and mixtures thereof.

11. A glove according to claim 1, wherein the liquid antiseptic composition further contains a viscosity-modifying polymer as a means for adjusting the viscosity of the liquid antiseptic composition to between about 1 centipoise and about 5000 centipoise at a temperature of between about 10 to about 45 degrees centigrade, the viscosity-modifying polymer selected from the group consisting of xantham gum, gum acacia, gum tragacanth, agar, glycyrrhiza, sodium alginate, cellulose, methyl cellulose, carboxymethylcellulose sodium, glycerol, propylene glycol, pyroxylin, polyoxyethylene glycols of about 150 to about 600 molecular weight, gelatin, dimethicone of about 100 to about 1000 centistokes viscosity, simethicone, dimethylpolysiloxane, perfluropolymethyl-isopropyl ether of about 1500 to about 6600 molecular weight, starch, and mixtures thereof.

12. A glove according to claim 1, wherein a structural connection is made by using a third material to connect the first material to the second material, the third material comprising:
(a) a structural material selected from the group consisting of latex rubber, cis-1,4-polyisoprene rubber, cis-polybutadiene rubber, neoprene rubber, nitrile rubber, silicone rubber, cellulose acetate plastic, vinyl plastic, polyethylene plastic, polypropylene plastic, polyvinyl chloride plastic, polyvinyl acetate plastic, polystyrene plastic, polymethyl methylacrylate plastic, polyacrylonitrile plastic, vinyllite plastic, saran plastic, polytetrafluoroethylene plastic, polytrifluorochloroethylene plastic, nylon plastic, rayon plastic, polycaprolactam plastic, polyester plastic, urea formaldehyde plastic, polyurethane plastic, isotactic polypropylene plastic, polyamide plastic, phenolic plastic, silicone plastic, silk fiber, cotton fiber, plant fiber, wool fiber, animal skin, animal intestinal tissue, animal connective tissue, metallic fiber, mineral fiber, a glue comprising at least one of the aforementioned structural materials, and mixtures thereof.

13. A glove according to claim 12, wherein the structural connection reconfigures the compartment storing the liquid antiseptic composition into a plurality of compartments capable of storing the liquid antiseptic composition.

14. A glove according to claim 1, wherein the liquid antiseptic composition comprises:
(a) about 0.02 to about 20 parts of povidone-iodine,
(b) about 0.1 to about 90 parts of water,
(c) about 0.05 to about 30 parts of a polyethylene glycol of about 150 to about 600 molecular weight, and
(d) about 0.1 to about 90 parts of an alcohol, the alcohol selected from the group consisting of ethanol, isopropanol, propanol, n-butanol, sec-butanol, tert-butanol, benzyl alcohol, methanol, and mixtures thereof.

15. A glove according to claim 1, wherein the liquid antiseptic composition comprises:
(a) about 0.1 to about 20 parts of elemental iodine,
(b) about 0.1 to about 20 parts of sodium iodide
(c) about 0.1 to about 30 parts of water,
(d) about 0.05 to about 30 parts of a polyethylene glycol of about 150 to about 600 molecular weight, and
(e) about 0.1 to about 90 parts of an alcohol, the alcohol selected from the group consisting of ethanol, isopropanol, propanol, n-butanol, sec-butanol, tert-butanol, benzyl alcohol, methanol, and mixtures thereof.

16. A glove according to claim 1, wherein the liquid antiseptic composition comprises:
(a) about 0.1 to about 35 parts of sodium hypochlorite,
(b) about 50 to 99 parts of water,
(c) about 0.05 to about 30 parts of a polyethylene glycol of about 150 to about 600 molecular weight, and (d) about 0.1 to about 90 parts of an alcohol, the alcohol selected from the group consisting of ethanol, isopropanol, propanol, n-butanol, sec-butanol, tert-butanol, benzyl alcohol, methanol, and mixtures thereof.

17. A glove according to claim 1, wherein the liquid antiseptic composition comprises;
   (a) about 0.1 to about 25 parts of chlorhexidine gluconate,
   (b) about 0.1 to about 90 parts of water,
   (c) about 0.05 to about 30 parts of a polyethylene glycol of about 150 to about 600 molecular weight, and
   (d) about 0.1 to about 90 parts of an alcohol, the alcohol selected from the group consisting of ethanol, isopropanol, propanol, n-butanol, sec-butanol, tert-butanol, benzyl alcohol, methanol, and mixtures thereof.

18. A glove according to claim 1, wherein the liquid antiseptic composition comprises;
   (a) about 0.1 to about 50 parts of nonoxynol-9,
   (b) about 0.1 to about 95 parts of water,
   (c) about 0.05 to about 30 parts of a polyethylene glycol of about 150 to about 600 molecular weight, and
   (d) about 0.1 to about 90 parts of an alcohol, the alcohol selected from the group consisting of ethanol, isopropanol, propanol, n-butanol, sec-butanol, tert-butanol, benzyl alcohol, methanol, and mixtures thereof.

19. A method of using a flexible protective glove with a liquid-impermeable wall on a hand of an individual to protect the hand in the event that an object contaminated with an infectious agent punctures the glove, may wound the hand and may contaminate the hand and the hand wound with the infectious pathogen, comprising the steps of:
   (a) using the glove initially as a liquid-impermeable physical barrier to infectious pathogens; using the glove to permit the hand to perform a delicate, dexterous and complex type of work that includes the type of work performed by a surgeon, medical doctor, a dentist, a laboratory worker, a hospital health care worker, a law enforcement worker, and a hospital worker; and storing a liquid antiseptic composition in the glove wall;
   (b) using the object to puncture the glove wall;
   (c) using the glove to coat a portion of the object puncturing the glove wall with the liquid antiseptic composition when the object punctures the compartment storing the liquid antiseptic composition;
   (d) using the object puncturing the glove to transfer a portion of the coating of the liquid antiseptic composition on the object, to the hand and into the hand wound when the object contacts the hand;
   (e) using the glove wall having the hole formed by the object as a means for leaking more liquid antiseptic composition from the glove wall onto the hand and into the hand wound than from the glove wall onto the outer surface of the glove;
   (f) controlling the relative size of the holes in the outer and inner glove layers to bias the direction of liquid antiseptic composition from the glove so that most of the leakage occurs across the inner glove layer onto the hand and into the hand wound rather than across the outer glove layer by selecting a material composition for the inner glove layer that is less elastic than the material composition selected for the outer glove layer; and
   (g) using the liquid antiseptic composition transferred from the glove to the hand and to the hand wound to kill, to inactivate, and to otherwise destroy the infectious pathogen that may have been transferred to the skin and into the hand wound by the object.

20. A flexible protective glove with a liquid-impermeable wall having the capability to provide a liquid antiseptic composition treatment to a hand and to a hand wound should the wound occur underneath the glove while the glove is being worn when a wall of the glove is punctured by an object that may be contaminated with an infectious pathogen, comprising:
   (a) a glove wall with a liquid-impermeable outer layer comprised of a first material having a thickness of about 1 mil to about 40 mils and a liquid-impermeable inner layer composed of a second material having a thickness of about 0.3 mil to about 30 mils wherein the first material and the second material form the layers of a compartment capable of storing a liquid antiseptic composition;
   (b) the liquid antiseptic composition which contains a vasoconstrictive agent;
   (c) the glove wall capable of providing a physical barrier as a means of protection to the hand while the glove is being worn by an individual; the glove wall capable of being punctured by the object;
   (d) the glove having the flexibility to allow the hand of the individual wearing the glove to easily and adequately perform delicate, dexterous and complex work including the work performed by a surgeon, medical doctor, a dentist, a laboratory worker, a health care worker, a law enforcement worker, a hospital worker and like workers;
   (e) the glove having the capability to provide a coating of liquid antiseptic composition to at least a portion of the object puncturing the glove wall; the coating of liquid antiseptic composition on the object providing a means for immediately transferring some liquid antiseptic composition onto the hand and into the hand wound contacted by the object; the liquid antiseptic composition transferred to the skin and to the hand wound having the capability to help to provide an immediate treatment of liquid antiseptic composition to the hand and to the hand wound;
   (f) the glove having the additional capability of leak some of the liquid antiseptic composition from a section of the glove wall having a hole resulting from the object puncturing the glove wall; the liquid antiseptic composition leaking from the hole having the capability to flow onto the hand and into the hand wound as a means for providing a treatment of liquid antiseptic composition to the hand and to the hand wound; and
   (g) the glove having the capability to help to treat the hand and the hand wound with a liquid antiseptic composition when the object punctures the glove wall, when the object may contact, when the object may wound the hand, and when the object may contaminate the hand and the hand wound with the infectious pathogen; wherein the liquid antiseptic composition transferred to the hand and to the hand wound has the capability to help to protect the hand, the hand wound and the systemic circulation of the individual by killing, inactivating, and otherwise destroying the infectious pathogen that may contaminate the hand and the hand wound.

* * * * *

UNITED STATES PATENT AND TRADEMARK OFFICE
CERTIFICATE OF CORRECTION

PATENT NO. : 5,335,373
DATED : August 9, 1994
INVENTOR(S) : Karl P. Dresdner, Jr et al It is certified that error appears in the above-indentified patent and that said Letters Patent is hereby corrected as shown below:

On the Title Page, under item [19], "Dangman" should be --Dresdner, Jr.--; and in item [76], as the first named inventor add Karl P. Dresdner, Jr.
Five Tudor City Place, Apt-2010
New York, New York 10017

Signed and Sealed this

Thirteenth Day of June, 1995

Attest:

BRUCE LEHMAN

Attesting Officer

Commissioner of Patents and Trademarks